US011561155B2

(12) United States Patent
Busse et al.

(10) Patent No.: US 11,561,155 B2
(45) Date of Patent: Jan. 24, 2023

(54) HEAVY METAL ION-HEMATEIN-COMPLEXES USEFUL AS EX VIVO CONTRAST AGENT FOR A COMPUTED TOMOGRAPHY SCANNING OF A BIOLOGICAL SAMPLE, EX VIVO METHOD FOR INVESTIGATING A BIOLOGICAL SAMPLE, AND USE OF THE COMPLEXES

(71) Applicant: TECHNISCHE UNIVERSITÄT MÜNCHEN, Munich (DE)

(72) Inventors: Madleen Busse, Eching (DE); Franz Pfeiffer, Unterföhring (DE)

(73) Assignee: TECHNISCHE UNIVERSITÄT MÜNCHEN, Munich (DE)

( * ) Notice: Subject to any disclaimer, the term of this patent is extended or adjusted under 35 U.S.C. 154(b) by 346 days.

(21) Appl. No.: 16/755,661

(22) PCT Filed: Oct. 12, 2018

(86) PCT No.: PCT/EP2018/077956
§ 371 (c)(1),
(2) Date: Apr. 13, 2020

(87) PCT Pub. No.: WO2019/073064
PCT Pub. Date: Apr. 18, 2019

(65) Prior Publication Data
US 2020/0271554 A1    Aug. 27, 2020

(30) Foreign Application Priority Data

Oct. 13, 2017  (EP) .................................... 17196491
Oct. 13, 2017  (EP) .................................... 17196492
Feb. 22, 2018  (EP) .................................... 18158168

(51) Int. Cl.
| | | |
|---|---|---|
| *G01N 1/30* | (2006.01) | |
| *C07F 3/00* | (2006.01) | |
| *C07F 5/00* | (2006.01) | |
| *C07D 311/00* | (2006.01) | |
| *C07D 311/94* | (2006.01) | |
| *G01N 23/046* | (2018.01) | |
| *C07F 1/10* | (2006.01) | |
| *C07F 7/24* | (2006.01) | |

(52) U.S. Cl.
CPC .......... *G01N 1/30* (2013.01); *C07D 311/00* (2013.01); *C07D 311/94* (2013.01); *C07F 3/00* (2013.01); *C07F 5/00* (2013.01); *G01N 23/046* (2013.01); *C07F 1/10* (2013.01); *C07F 7/24* (2013.01); *G01N 2001/302* (2013.01); *G01N 2001/305* (2013.01)

(58) Field of Classification Search
None
See application file for complete search history.

(56) References Cited

FOREIGN PATENT DOCUMENTS

WO    2007089641 A2    8/2007

OTHER PUBLICATIONS

International Search Report for International Application No. PCT/EP2018/077956, dated Jan. 14, 2019 (12 pages).
Extended European Search Report for European Application No. 17196491.9, dated Mar. 27, 2018 (6 pages).
Extended European Search Report for European Application No. 17196492.7, dated Apr. 24, 2018 (12 pages).
Database Caplus, Chemical Abstracts Service, Columbus, Ohio, XP-002779072, retrieved from STN, Database accession No. 2012:416299, 2012, (2 pages).
Baker, "Experiments on the Action of Mordants 2. Aluminium-Haematein", Journal of Cell Science, pp. 493-517, Dec. 1, 1962, (26 pages).
Suarez et al., "Inversion of stereoselectivity in 1,3-butadiene polymerization with a niobium catalyst induced by a change in the solvent system", Polymer Bulletin, vol. 41, No. 2, pp. 175-182, Aug. 1, 1998, (8 pages).
Suarez et al., "Stereoselectivity in 1-3-butadiene polymerization using new titanium chelates", Polymer Bulletin, vol. 39, No. 3, pp. 311-315, Sep. 1, 1997, (6 pages).
Database Caplus, Chemical Abstracts Service, Columbus, Ohio, XP-002779073, retrieved from STN, Database accession No. 1984:582843, 1984, (1 pages).
Kim et al., "Lip cosmetic composition having color lasting effect and method for preparing same", Database CA, Chemical Abstracts Service, Columbus, Ohio, XP-002780067, retrieved from STN, Database accession No. 2016:470465, 2016, (2 pages).
Qu et al., "Synthesis, characterization, antitumour and antibacterial activity of rare earth metal (III) solid complexes with tetraiodofluorescein", Database CA, Chemical Abstracts Service, Columbus, Ohio, XP-002780068, retrieved from STN, Database accession No. 2002:445434, 2002, (2 pages).

(Continued)

*Primary Examiner* — Joseph R Kosack
(74) *Attorney, Agent, or Firm* — Kagan Binder, PLLC

(57) ABSTRACT

The present invention relates to specific complexes comprising heavy metal ions having an atomic number of 23 or higher and 83 or lower (in particular $Ag^{1+}$, $Ba^{2+}$, $Pb^{2+}$, $Gd^{3+}$ and $Bi^{3+}$) and one or more hematein ligand(s). In particular, the invention relates to the use of the complexes as ex vivo contrast agents for a computed tomography scanning of a biological sample. Moreover, the invention relates to specific ex vivo methods for investigating a biological sample by means of computed tomography scanning methods, wherein the method comprises staining the biological sample with a solution comprising one or more of the complex(es); or wherein the method comprises staining the biological sample with a staining solution comprising hematein, and separately contacting the biological sample with one or more staining solution(s) comprising one or more heavy metal ions having an atomic number of 23 or higher and 83 or lower (in particular $Ag^{1+}$, $Ba^{2+}$, $Pb^{2+}$, $Gd^{3+}$ and $Bi^{3+}$).

21 Claims, 6 Drawing Sheets

(56) References Cited

OTHER PUBLICATIONS

Qu et al., "Complexes of tetraiodofluorescein with some transition metals and their antitumour activity", Database CA, Chemical Abstracts Service, Columbus, Ohio, XP-002780069, retrieved from STN, Database accession No. 2002:445433, 2002, (2 pages).

Agarwal et al., "Eosine and its metal complexes", Database CA, Chemical Abstracts Service, Columbus, Ohio, XP-002780070, retrieved from STN, Database accession No. 1980:460122, 1980, (2 pages).

Nakamura et al., "Lanthanide(III)-Hematein Complexes as Stain of Tissues for Medical Applications," International Journal of Current Chemistry, vol. 2, No. 4, pp. 243-252, Oct.-Dec. 2011, (10 pages).

El-Askalany et al., "Stability Constants of Zn(II), Pb(II), Cd(II) and Cu(II) Complexes with Hematoxylin", Chem. Pharm. Bull, 1995, 43(1), pp. 1791-1792, (2 pages).

Smith, A.A., "Specific staining of tissue components with metal-hematoxylin complexes", Micron 33, 2002, pp. 95-103, (9 pages).

Ashton et al., "In vivo small animal micro-CT using nanoparticle constrast agents", Frontiers on Pharmacology, vol. 6, Article 256, published Nov. 4, 2015, (22 pages).

Metscher, "MicroCT for comparative morphology: simple staining methods allow high-contrast 3D imaging of diverse non-mineralized animal tissues", BMC Physiology, 9:11, Published Jun. 22, 2009, (14 pages).

Hopkins et al., "Combining micro-computed tomography with histology to analyze biomedical implants for peripheral nerve repair", Journal of Neuroscience Methods, pp. 122-130, 2015, (9 pages).

"Masson's trichrome stain", retrieved from https://en.wikipedia.org/wiki/Masson%27s_trichrome_stain, (1 page).

"Masson's Connective Tissue Stain", retrieved from doctorc.net/Labs/Lab2/Examples/exmasson.htm, (1 page).

"Nuclear Science Abstracts, Band 18, Ausgaben 13-19", (1 page).

European Patent Office, "Communication Pursuant to Article 94(3) EPC", issued in connection with European application No. 18783037.7 dated Apr. 8, 2021, (4 pages).

Miyagawa, "Histochemical Stains for Minerals by Hemotoxylin-Lake Method", Medical Online, 61:4, pp. 314-317, 2013, (5 pages).

Huang et al.,"Spectroscopic investigations of interactions between Hemotoxylin-Ag complex and Herring-sperm DNA with the aid of the acridine orange probe", Journal of Molecular Structure, pp. 73-78, 2012, (6 pages).

Dubsky, J. et al., "Chemicke Listy", Reaxys, vol. 34, p. 137-139, 1940, (3 pages).

(a)        (b)

(a)        (b)

(a)        (b)

Figure 4
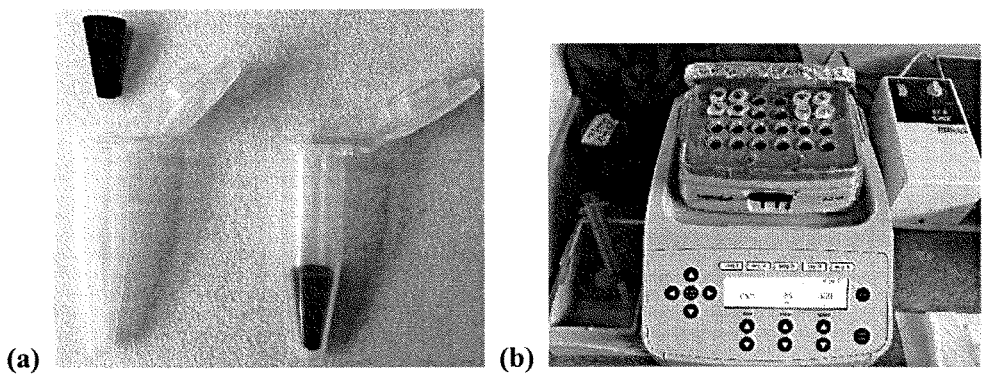
Figure 5
(a)
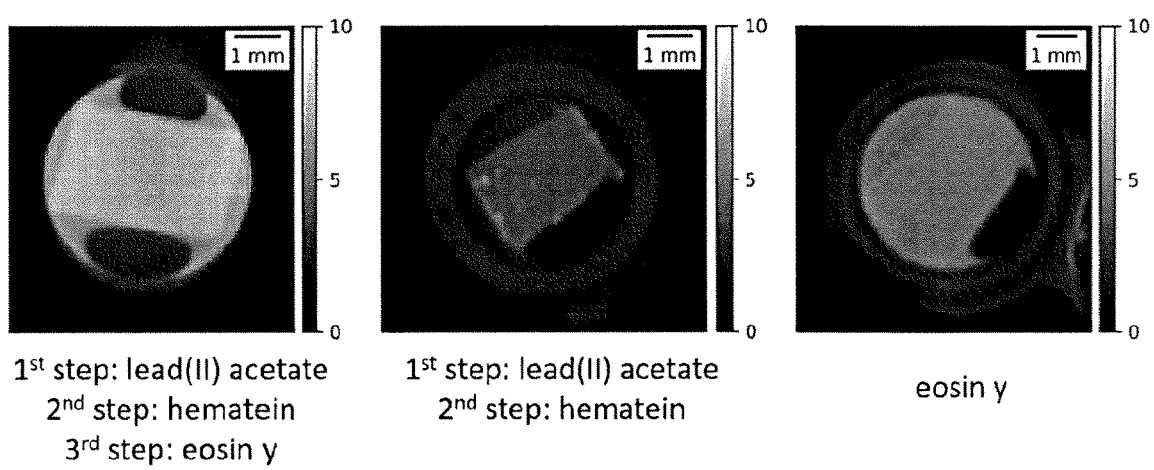
1st step: lead(II) acetate
2nd step: hematein
3rd step: eosin y
1st step: lead(II) acetate
2nd step: hematein
eosin y
(b)
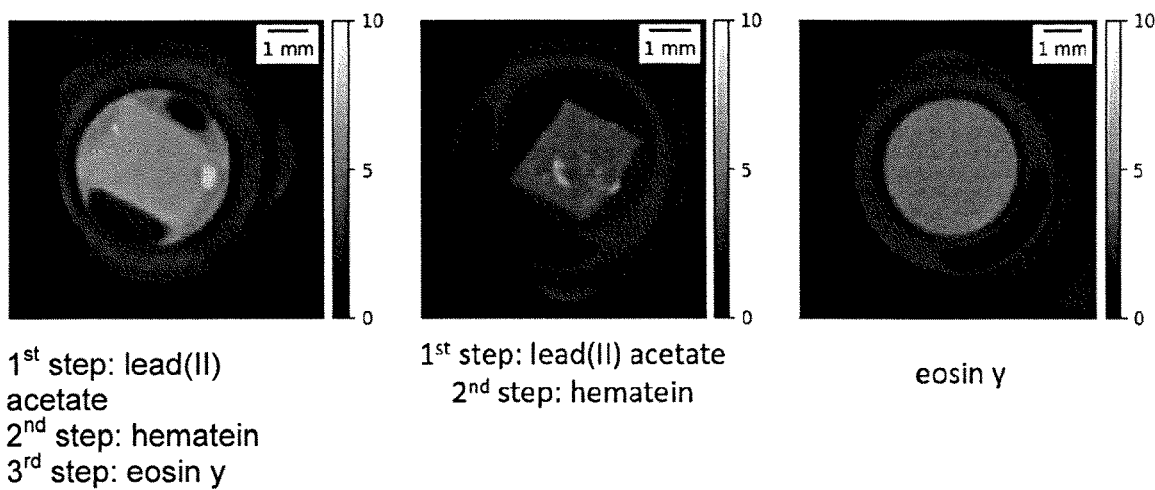
1st step: lead(II) acetate
2nd step: hematein
3rd step: eosin y
1st step: lead(II) acetate
2nd step: hematein
eosin y

Figure 5 (continued)
(c)
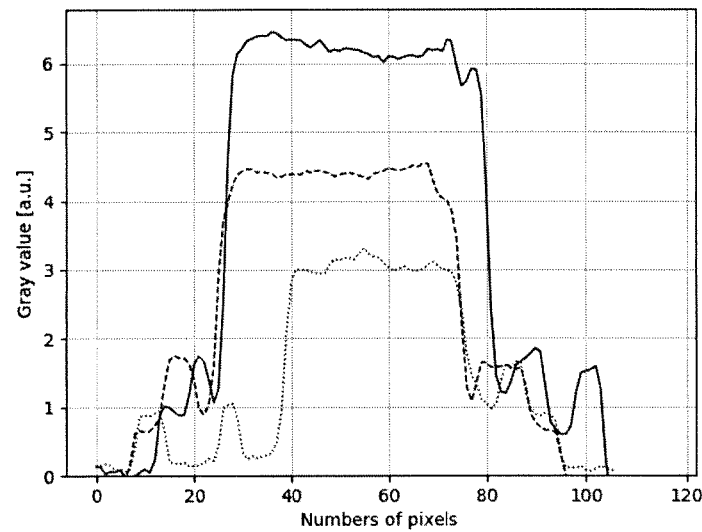
(d)
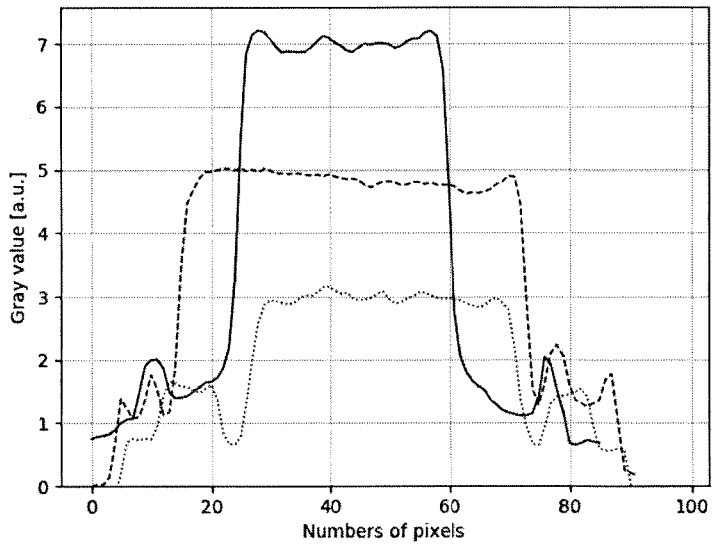

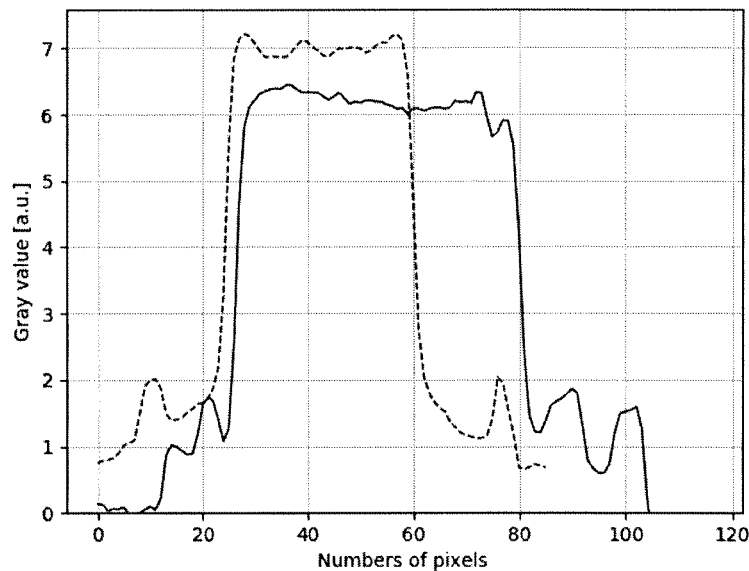

Figure 6

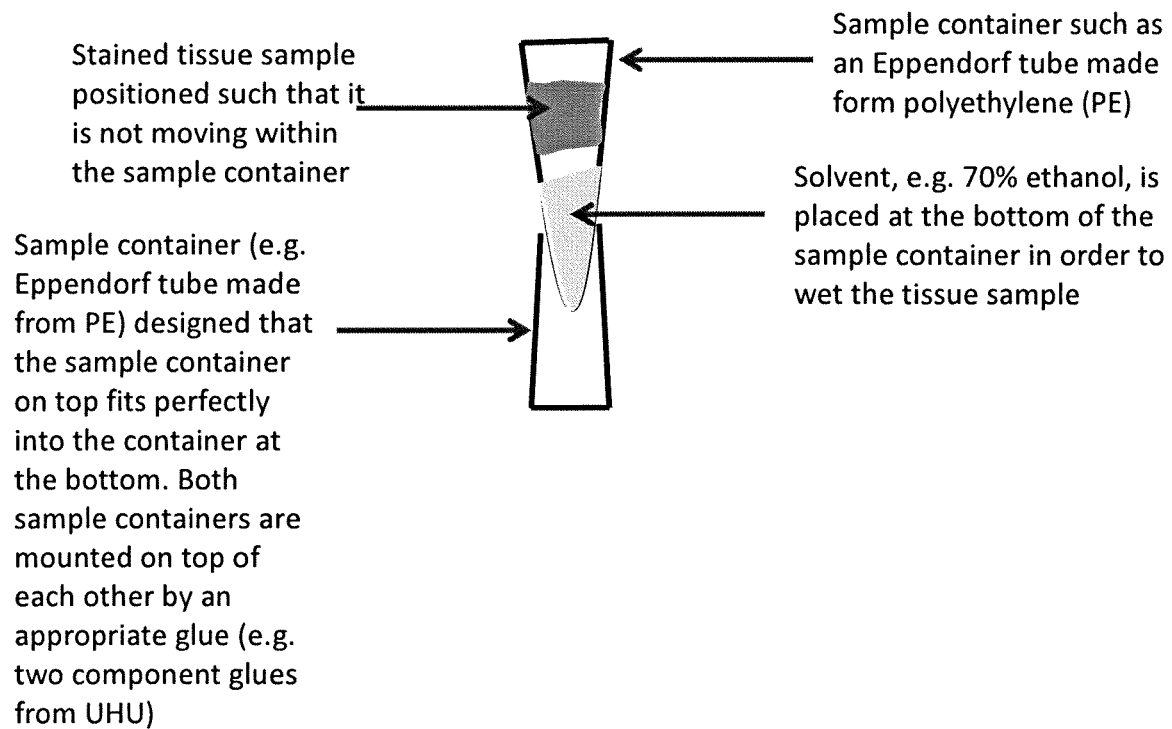

Stained tissue sample positioned such that it is not moving within the sample container Sample container (e.g. Eppendorf tube made from PE) designed that the sample container on top fits perfectly into the container at the bottom. Both sample containers are mounted on top of each other by an appropriate glue (e.g. two component glues from UHU)

Sample container such as an Eppendorf tube made form polyethylene (PE)

Solvent, e.g. 70% ethanol, is placed at the bottom of the sample container in order to wet the tissue sample (a) (b) (c)

(a) (b)

HEAVY METAL ION-HEMATEIN-COMPLEXES USEFUL AS EX VIVO CONTRAST AGENT FOR A COMPUTED TOMOGRAPHY SCANNING OF A BIOLOGICAL SAMPLE, EX VIVO METHOD FOR INVESTIGATING A BIOLOGICAL SAMPLE, AND USE OF THE COMPLEXES

CROSS-REFERENCE TO RELATED APPLICATIONS

This application claims priority to International Application No. PCT/EP2018/077956, filed Oct. 12, 2018 and titled "NOVEL HEAVY METAL ION-HEMATEIN-COMPLEXES USEFUL AS EX VIVO CONTRAST AGENT FOR A COMPUTED TOMOGRAPHY SCANNING OF A BIOLOGICAL SAMPLE, EX VIVO METHOD FOR INVESTIGATING A BIOLOGICAL SAMPLE, AND USE OF THE COMPLEXES," which in turn claims priority from European Patent Application serial number 17196491.9, filed Oct. 13, 2017, titled "NOVEL HEAVY METAL ION-LIGAND-COMPLEXES USEFUL AS EX VIVO CONTRAST AGENT FOR A COMPUTED TOMOGRAPHY SCANNING OF A BIOLOGICAL SAMPLE, EX VIVO METHOD FOR INVESTIGATING A BIOLOGICAL SAMPLE, AND USE OF THE COMPLEXES;" European Patent Application serial number 17196492.7, filed Oct. 13, 2017, titled "NOVEL HEAVY METAL ION-LIGAND-COMPLEXES USEFUL AS EX VIVO CONTRAST AGENT FOR A COMPUTED TOMOGRAPHY SCANNING OF A BIOLOGICAL SAMPLE, EX VIVO METHOD FOR INVESTIGATING A BIOLOGICAL SAMPLE, AND USE OF THE COMPLEXES;" and European Patent Application serial number 18158168.7, filed Feb. 22, 2018, titled "NOVEL HEAVY METAL ION-LIGAND-COMPLEXES USEFUL AS EX VIVO CONTRAST AGENT FOR A COMPUTED TOMOGRAPHY SCANNING OF A BIOLOGICAL SAMPLE, EX VIVO METHOD FOR INVESTIGATING A BIOLOGICAL SAMPLE, AND USE OF THE COMPLEXES," all of which are incorporated herein by reference in their entireties.

TECHNICAL FIELD

The present invention relates to specific complexes comprising heavy metal ions having an atomic number of 23 or higher and 83 or lower (in particular $Ag^{1+}$, $Ba^{2+}$, $Pb^{2+}$, $Gd^{3+}$ and $Bi^{3+}$) and one or more hematein ligand(s). In particular, the invention relates to the use of the complexes as contrast agents for a computed tomography scanning of a biological sample. Moreover, the invention relates to specific ex vivo methods for investigating a biological sample by means of computed tomography scanning methods, wherein the method comprises staining the biological sample with a solution comprising one or more of the complex(es); or (herein below sometimes referred to as in situ staining) wherein the method comprises staining the biological sample with a staining solution comprising hematein, and separately contacting the biological sample with one or more staining solution(s) comprising one or more heavy metal ions having an atomic number of 23 or higher and 83 or lower (in particular $Ag^{1+}$, $Ba^{2+}$, $Pb^{2+}$, $Gd^{3+}$ and $Bi^{3+}$).

BACKGROUND

The study of tissue is known as histology or, in connection with disease, histopathology. The conventional tools for studying tissues are the paraffin block in which tissue is embedded and then sectioned, the histological stain, and the optical microscope. In the last decades, amongst others, the use of frozen tissue sections has enhanced the detail that can be observed in tissues. With these tools, the appearances of tissues can be examined in health and disease, enabling medical diagnosis and prognosis.

Many conventional histological methods require specific staining of the cell nucleus (in particular, bind to the chromatin of the nuclei of cells), which provides instrumental details for diagnosis. Currently, hematein-based stains are the most commonly used cell nucleus contrast agents (CAs) and are used as counter stains (e.g., in case of eosin staining) in conventional histology. Many of the standard staining methods used in conventional histology today still trace back to the founding fathers of histological staining. Important examples are the hemalaun by Mayer (1920), Harris (1900), Ehrlich (1886) and Delafield (1885), as well as the iron-based hemalaun by Heidenhain (1892) and Weigert (1904) (cf. M. Mulisch and U. Welsch, Romeis Mikroskopische Technik, 19th Ed. Springer Spektrum, Heidelberg, 2015, 187-193). A summary of the afore-mentioned staining methods and their respective characteristics is given by Mulisch and Welsch (M. Mulisch and U. Welsch, Romeis Mikroskopische Technik, 19th Ed. Springer Spektrum, Heidelberg, 2015, p. 189, table 10.1).

One major limitation of conventional histological methods, which are frequently used for diagnostic purposes in a clinical setting, is the production of two-dimensional (2D) images obtained by destructive preparation of a three-dimensional (3D) tissue sample. The destructive preparation in conventional histological methods is obligatory since thin tissue sections (generally 2 to 10 μm thick) have to be prepared since only these sections can be adequately assessed by (light) microscopic methods. The preparation of the afore-mentioned tissue sections is not only time-consuming, but also interrelated to an information loss which considerably limits the diagnostic potential of conventional histology. As an illustrative example, reference is made to a 1×1×1 mm histological sample. The slices produced in conventional histology can vary but a thickness of about 2 μm is commonly used. This, however, were to result in about 500 sections if the entire biological sample were to be investigated. When looking at the daily reality of a histologist/pathologist who has to inspect about 500 biological samples per day, it is evident that only a few microscopic slices per biological sample are prepared and can be investigated.

X-ray imaging techniques such as computed tomography (CT), in particular Micro-Computed Tomography (μCT), allow for a non-destructive investigation of a 3D biological samples enabling sample screening, and thus, aid to determine regions of interest for further histological examinations. Within a short period of time (usually about 2 hours) a complete tomography is obtained which provides 3D information for the entire biological sample. During this period of time about 1000 slices are produced for each viewing plane (xy, yz, xz).

At present, however, the application of CT (in particular μCT) for biological samples is severely limited by the missing contrast of many biological samples (in particular soft tissue samples). A sufficient contrast, however, is important to visualize morphological details. While there are some CAs for CT applications described in the prior art such as iodine potassium iodide (IKI), iodine in ethanol ($I_2E$) and phosphotungstic acid (PTA) (Metscher, B. D. (2009). MicroCT for comparative morphology: simple staining methods allow high-contrast 3D imaging of diverse non-mineralized animal tissues. BMC Physiology, 9, 1-14; Martins de Souza e Silva, J. et al. (2015). Three-dimensional non-destructive soft-tissue visualization with X-ray staining micro-tomography. Scientific Reports, 5, 14088.), the quality of the tomography/tomographic images obtainable with the prior art CAs is limited. In particular, it is very challenging to obtain a homogeneous staining result with the prior art CAs/staining methods. Moreover, compatibility of the prior art CAs with conventional histological methods is not always given. In view of this, there is a need for further improvement of the existing CAs and the staining methods described in the prior art.

In view of the above, it is an object of the present invention to overcome one or more of the disadvantages of the prior art CAs/staining methods.

SUMMARY

The present inventors surprisingly found novel CAs as well as novel staining methods which can provide a contrast enhancement in CT investigations of biological samples. This, in turn, can facilitate the provision of highly detailed 3D structural information of the investigated biological sample, which—amongst others—aid to determine regions of interest. Moreover, the inventive CAs are compatible with conventional histological methods so that a further investigation of regions of interest with conventional histological methods is possible (see for example FIGS. 5 and 6). In preferred embodiments, it is possible to obtain homogeneous staining results throughout the whole biological sample. Additionally, in some embodiments, the inventive staining methods allow for the use of easy reducible heavy metals (e.g. $Ag^+$) in hematein-based staining.

In particular, the present invention relates to the following items 1 to 55:
1. A complex comprising:
one or more heavy metal ion(s) M and one or more ligand(s) R, wherein
at least one M is a heavy metal ion having an atomic number of 23 or higher and 83 or lower, and
at least one R is hematein.
2. The complex according to item 1, wherein the complex is represented by the following formula (I):

$$M_m R_n \quad (I),$$

in which at least one M is a heavy metal ion having an atomic number of 23 or higher and 83 or lower,
at least one R is hematein, and
m and n are each independently 1, 2, 3, 4, 5, 6, 7, 8, 9, 10, 11 or 12.
3. The complex according to item 1 or 2, wherein
at least one of the one or more heavy metal ions(s) M is a heavy metal ion having an atomic number of 27 or higher and 83 or lower, and
m and n are each independently 1, 2 or 3.
4. The complex according to any one of items 1 to 3, wherein m and n are both 1.
5. The complex according to any one of items 1 to 4, wherein
at least one of the one or more heavy metal ion(s) M is an ion of a heavy metal selected from the group consisting of silver (Ag), barium (Ba), lead (Pb), gadolinium (Gd), bismuth (Bi), lutetium (Lu) and lanthanum (La) (preferably barium (Ba)).
6. The complex according to item 5, wherein
at least one of the one or more heavy metal ion(s) M is selected from the group consisting of silver(I) ($Ag^{1+}$), barium(II) ($Ba^{2+}$), lead(II) ($Pb^{2+}$), gadolinium(III) ($Gd^{3+}$), bismuth(III) ($Bi^{3+}$), lutetium(III) ($Lu^{3+}$) and lanthanum(III) ($La^{3+}$).
7. The complex according to item 6, wherein
at least one of the one or more heavy metal ion(s) M is selected from the group consisting of $Ag^{1+}$, $Ba^{2+}$, $Pb^{2+}$, $Gd^{3+}$ and $Bi^{3+}$ (preferably $Ba^{2+}$).
8. The complex according to item 6, wherein
at least one of the one or more heavy metal ion(s) M is selected from the group consisting of $Ag^{1+}$, $Ba^{2+}$, $Pb^{2+}$ and $Gd^{3+}$.
9. The complex according to item 6, wherein
at least one of the one or more heavy metal ion(s) M is $Ag^{1+}$.
10. The complex according to item 6, wherein
at least one of the one or more heavy metal ion(s) M is $Ba^{2+}$.
11. The complex according to item 6, wherein
at least one of the one or more heavy metal ion(s) M is $Pb^{2+}$.
12. The complex according to item 6, wherein
at least one of the one or more heavy metal ion(s) M is $Gd^{3+}$.
13. The complex according to item 6, wherein
at least one of the one or more heavy metal ion(s) M is $Bi^{3+}$.
14. The complex according to item 6, wherein
at least one of the one or more heavy metal ion(s) M is $Lu^{3+}$.
15. The complex according to item 6, wherein
at least one of the one or more heavy metal ion(s) M is $La^{3+}$.
16. An ex vivo method for investigating a biological sample comprising
(aspect 1)
(a1) staining the biological sample with a solution (AB) comprising one or more complex(es) as defined in any one of items 1 to 15; and
(b) subjecting the stained biological sample to a computed tomography scanning method;
or (aspect 2)
(a2) staining the biological sample with
(i) a solution (A) comprising hematein, and
(ii) one or more solution(s) (B) comprising one or more heavy metal ion(s) as defined in any one of items 1 to 3 and 5 to 15,
wherein the biological sample is contacted with solution (A) separately from the one or more solution(s) (B); and
(b) subjecting the stained biological sample to a computed tomography scanning method.
17. The method according to item 16 (aspect 1/aspect 2), wherein the computed tomography scanning method is an absorption-based scanning method.
18. The method according to item 16 (aspect 1/aspect 2) or 17, wherein the computed tomography scanning method is an X-ray absorption-based scanning method.
19. The method according to any one of items 16 (aspect 1/aspect 2), 17 and 18, wherein the computed tomography scanning method is selected from the group consisting of Micro-Computed Tomography (μCT) and Nano-Computed Tomography (nanoCT).
20. The method according to item 19, wherein the computed tomography scanning method is μCT.
21. The method according to item 19, wherein the computed tomography scanning method is nanoCT.
22. The method according to any one of items 16 (aspect 1/aspect 2) and 17 to 21, wherein the biological sample is a soft tissue sample.
23. The method according to any one of items 16 (aspect 1/aspect 2) and 17 to 22, wherein the biological sample is a human soft tissue sample.

24. The method according to any one of items 16 (aspect 1/aspect 2) and 17 to 23, wherein the biological sample originates from lung, kidney, liver, brain, spleen, heart or cartilage.

25. The method according to any one of items 16 (aspect 1/aspect 2) and 17 to 24, wherein the biological sample is subjected to chemical fixation by means of one or more chemical fixative(s) prior to staining.

26. The method according to item 25, wherein the one or more chemical fixative(s) is/are a water-based formaldehyde solution or a water-based glutaraldehyde solution, or mixtures thereof.

27. The method according to item 25, wherein the one or more chemical fixative(s) is/are a formaldehyde solution in Dulbecco's phosphate buffered saline or a formaldehyde solution in phosphate buffered saline.

28. The method according to any one of items 25 to 27, wherein the one or more chemical fixative(s) comprise one or more acid(s).

29. The method according to item 28, wherein the one or more acid(s) is glacial acetic acid.

30. The method according to any one of items 16 (aspect 1/aspect 2) and 17 to 29, wherein the method comprises, in addition to staining step (a1) or staining step (a2) an additional step of staining with an additional staining agent.

31. The method according to item 30, wherein the additional staining agent is a xanthene derivative (preferably selected from the group consisting of mono-, di-, tribromofluorescein; mono-, di, triiodofluorescein; eosin B; eosin Y and erythrosine B).

32. The method according to any one of items 16 (aspect 1/aspect 2) and 17 to 31, wherein the concentration of complex-bound hematein in solution (AB) or of hematein in solution (A) is in the range of about 150 to about 500 mM.

33. The method according to item 32, wherein the concentration of complex-bound hematein in solution (AB) or of hematein in solution (A) is in the range of about 200 to about 450 mM.

34. The method according to item 32, wherein the concentration of complex-bound hematein in solution (AB) or of hematein in solution (A) is in the range of about 250 to about 400 mM.

35. The method according to item 32, wherein the concentration of complex-bound hematein in solution (AB) or of hematein in solution (A) is in the range of about 300 to about 400 mM.

36. The method according to item 32, wherein the concentration of complex-bound hematein in solution (AB) or of hematein in solution (A) is in the range of about 300 to about 350 mM.

37. The method according to any one of items 16 (aspect 2) and 17 to 36, wherein the time period of contacting the biological sample with solution (A) or the one or more solution(s) (B) is 1 hour or more.

38. The method according to item 37, wherein the time period is 3 hours or more.

39. The method according to item 37, wherein the time period is 6 hours or more.

40. The method according to item 37, wherein the time period is 12 hours or more.

41. The method according to item 37, wherein the time period is 24 hours or more.

42. The method according to item 37, wherein the time period is 48 hours or more.

43. The method according to item 37, wherein the time period is 96 hours or more.

44. The method according to item 37, wherein the time period is 168 hours or more.

45. The method according to any one of items 16 (aspect 2) and 17 to 44, wherein the biological sample is contacted with solution (A) before the biological sample is contacted with the one or more solution(s) (B).

46. The method according to any one of items 16 (aspect 2) and 17 to 44, wherein the biological sample is contacted with the one or more solution(s) (B) before the biological sample is contacted with solution (A).

47. The method according to any one of items 16 (aspect 2) and 17 to 46, wherein the main solvent of solution (A) is different to the main solvent of the one or more solution(s) (B).

48. The method according to item 47, wherein the main solvent of solutions (A) is ethanol, and the main solvent of the one or more solution(s) (B) is a water-based solution.

49. The method according to any one of items 16 (aspect 1/aspect 2), 17 to 29 and 32 to 48, wherein the method does not comprise, in addition to staining step (a1) or staining step (a2), an additional step of staining with an additional staining agent.

50. Use of a complex according to any one of items 1 to 15 as an ex vivo contrast agent for a computed tomography scanning of a biological sample.

51. The use according to item 50, wherein the computed tomography scanning is an absorption-based scanning method.

52. The use according to item 50 or 51, wherein the computed tomography scanning is an X-ray absorption-based scanning method.

53. The use according to any one of items 50 to 52, wherein the computed tomography scanning method is selected from the group consisting of µCT and nanoCT.

54. The use according to item 53, wherein the computed tomography scanning method is µCT.

55. The use according to item 53, wherein the computed tomography scanning method is nanoCT.

In particularly preferred embodiment, the present invention relates to:

An ex vivo method for investigating a biological sample comprising
  (a) staining the biological sample with
    (i) a solution (A) comprising hematein, and
    (ii) one or more solution(s) (B) comprising one or more heavy metal ion(s) M,
  wherein the biological sample is contacted with solution (A) separately from the one or more solution(s) (B); and
  (b) subjecting the stained biological sample to a computed tomography scanning method;
wherein the time period of contacting the biological sample with solution (A) or the one or more solution(s) (B) is 3 hours or more,
wherein the biological sample is a human sample,
wherein the concentration of hematein in solution (A) is in the range of about 250 to about 400 mM,
wherein the method comprises, in addition to staining step (a) an additional step of staining with an additional staining agent, preferably a xanthene derivative, more preferably a xanthene derivative selected from the group of mono-, di-, tribromofluorescein; mono-, di, triiodofluorescein; eosin B; eosin Y and erythrosine B, most preferably eosin Y or erythrosine B,
wherein M is a heavy metal ion selected from the group consisting of silver(I) ($Ag^{1+}$), barium(II) ($Ba^{2+}$), lead(II)

($Pb^{2+}$), gadolinium(III) ($Gd^{3+}$), bismuth(III) ($Bi^{3+}$), lutetium (III) ($Lu^{3+}$) and lanthanum(III) ($La^{3+}$), preferably $Ag^{1+}$, $Ba^{2+}$, $Pb^{2+}$ or $Gd^{3+}$.

BRIEF DESCRIPTION OF THE DRAWINGS

The invention is also illustrated by the following illustrative figures.

FIG. 4: (a) Sample holder used for the soft tissue sample staining described in example 4. (b) Shaker (ThermoMixer from Eppendorf) used for soft tissue sample staining described in example 4.

FIG. 5: (a) Representative CT slice showing the stained pig liver samples stained with the protocol mentioned in Example 4 at 25° C. (b) Representative CT slice showing the stained pig liver samples stained with the protocol mentioned in Example 4 at 35° C. (c) Line plots showing the results obtained with staining conditions applied in example 4 at 25° C. in comparison to the individually applied staining protocols of "in situ" lead(II)-hematein complex and eosin y complex (CT slices in (a); sample holder in FIG. 4a and Thermomixer form Eppendorf in FIG. 4b). (d) Line plots showing the results obtained with staining conditions applied in Example 4 at 35° C. in comparison to the individually applied staining protocols of "in situ" lead(II)-hematein complex and eosin y complex (CT slices in (b); sample holder in FIG. 4a and Thermomixer form Eppendorf in FIG. 4b). (e) Comparison of the line plots obtained for soft tissue samples at two different temperatures (25° C. and 35° C.) (individual CT slices in (a) for 25° C. and in (b) for 35° C.; sample holder in FIG. 4a and Thermomixer from Eppendorf in FIG. 4b).

Legend to (c): All soft tissue samples were stained at 25° C.

Black line: Lead(II) acetate was applied in the $1^{st}$ staining step, hematein in the $2^{nd}$ staining step and eosin y in the $3^{rd}$ and final staining step was applied.

Dashed line: Soft tissue sample was stained with eosin y only.

Dotted line: Soft tissue sample was stained with the "in situ" procedure described in example 2.

Legend to (d): All soft tissue samples were stained at 35° C.

Black line: Lead(II) acetate was applied in the $1^{st}$ staining step, hematein in the $2^{nd}$ staining step and eosin y in the $3^{rd}$ and final staining step was applied.

Dashed line: Soft tissue sample was stained with eosin y only.

Dotted line: Soft tissue sample was stained with the "in situ" procedure described in example 2.

Legend to (e): Comparison of soft tissue samples stained at 25° C. or 35° C.

Black line: Soft tissue sample was stained with lead(II) acetate in the $1^{st}$ staining step, hematein in the $2^{nd}$ staining step and eosin y in the $3^{rd}$ and final staining step at 25° C.

Dashed line: Soft tissue sample was stained with lead(II) acetate in the $1^{st}$ staining step, hematein in the $2^{nd}$ staining step and eosin y in the $3^{rd}$ and final staining step at 35° C.

Figure 7:
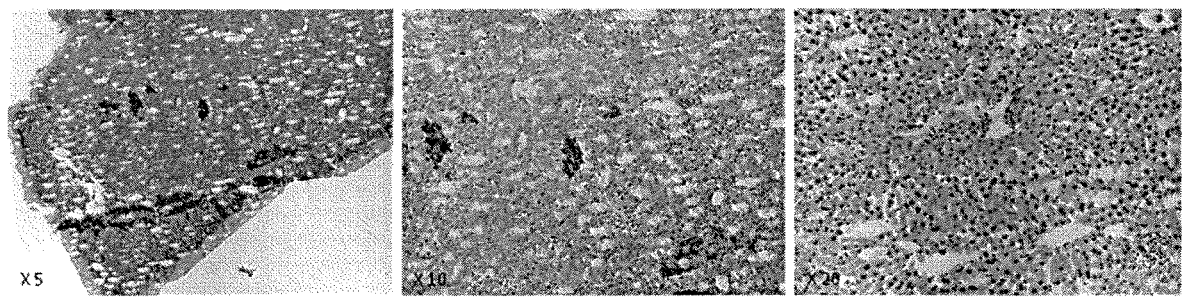

FIG. 6: Schematic drawing of a biological sample placed in an appropriate container for computed tomography scanning FIG. 7: 2D histological microscopic slice at different magnifications (5, 10 and 20-fold, respectively) of the mouse liver tissue prepared as described in example 2(a), i.e, being stained with lead(II) acetate as metal source and hematein as ligand (heavy metal:ligand ratio of 1:1). No further manipulations (except the preparation of the 2D histological microscopic slice) through the histologist were performed. The histological investigations show that the lead(II) hematein complex has formed in situ as evident from the tissue showing the dark blue to purple color characteristic to the lead(II)-hematein complex.

Figure 8:
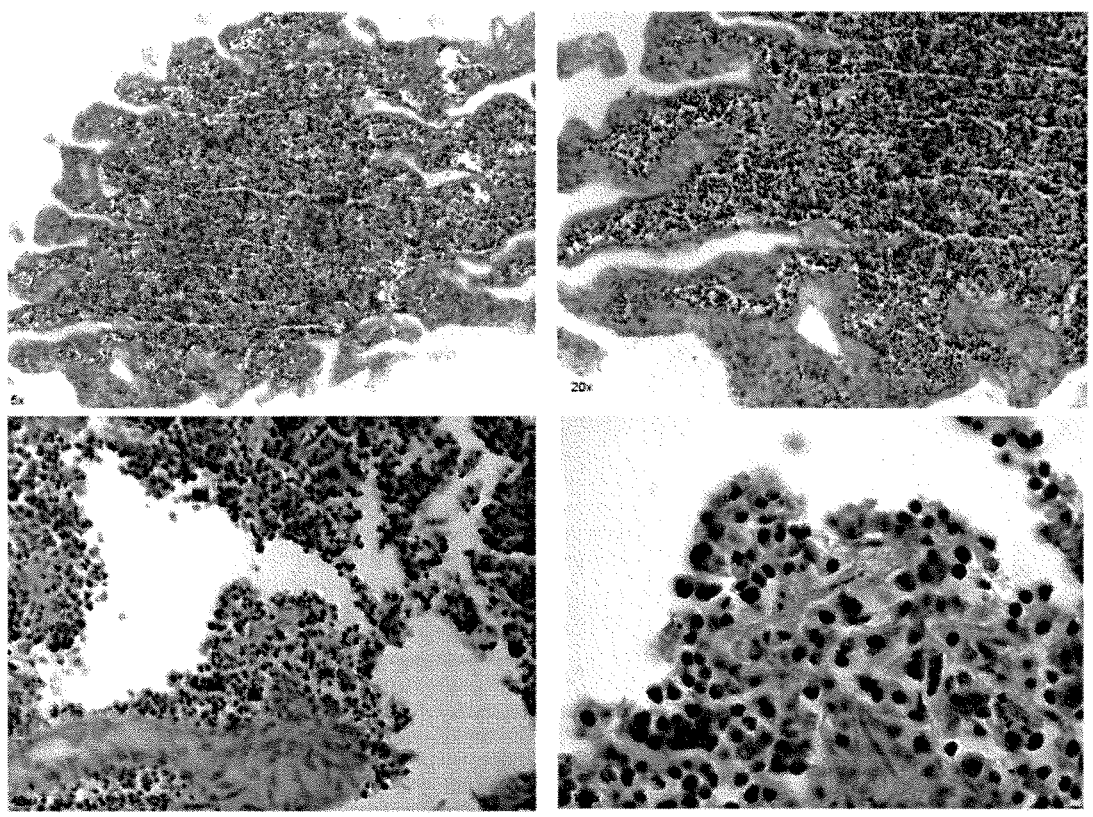

FIG. 8: 2D histological microscopic slice at different magnifications (5, 20, 40 and 100-fold, respectively; starting clockwise from the top left) of the mouse liver tissue prepared as described in example 2(a), i.e., being stained with lead(II) acetate as metal source and hematein as ligand (heavy metal:ligand ratio of 1:1). The 2D histological microscopic slice was counter stained afterwards with eosin. Even after counter staining with eosin the dark blue to purple color characteristic to the lead(II)-hematein complex is clearly visible. This shows full compatibility of the lead(II)-hematein complex with 2D histology and allows for further histological investigations.

Figure 9:
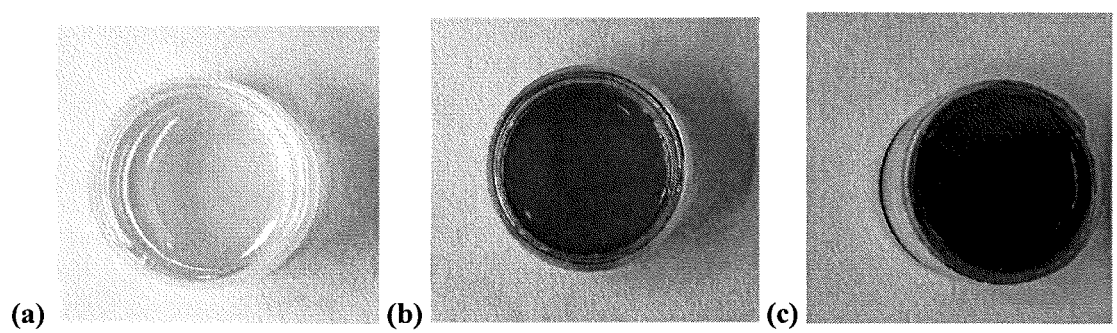

FIG. 9: Macroscopic images of various staining solutions. A freshly made lead(II) acetate solution is transparent as can be seen from FIG. 7(a). A ripened hematoxylin solution containing hematein is amber in color as shown in FIG. 7(b). Only the lead(II)-hematein complex is dark blue to purple in color (cf. FIG. 7(c)).

Figure 10:
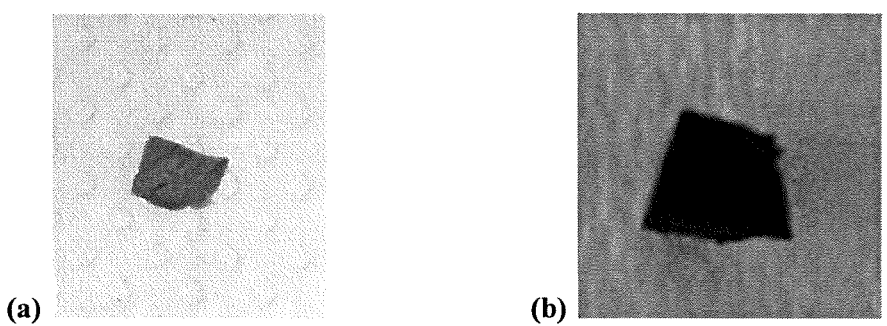

FIG. 10: Macroscopic images of the mouse liver sample stained in accordance with the "in situ" staining method described in Example 2. The tissue sample incubated in the transparent lead(II) acetate solution showed no substantial color change (cf. FIG. 8(a)). In contrast, upon incubation with the hematein solution in the $2^{nd}$ step resulted in a tissue sample having the characteristic dark blue to purple color of the lead(II)-hematein complex.

DETAILED DESCRIPTION

The following explanations of terms and methods are provided to better describe the present invention. Unless explained otherwise, all technical and scientific terms used herein have the same meaning as commonly understood by the skill person in the art to which this invention belongs. In case of conflict, the present description, including explanations of terms, will control.

Explanation of common terms and methods in the preparation, staining and microscopic investigation of biological samples (in particular tissue samples) may be found in Mulisch and Welsch (M. Mulisch and U. Welsch, Romeis Mikroskopische Technik, 19th Ed. Springer Spektrum Akademischer Verlag, Heidelberg, 2010), Murphy and Davidson (D. B. Murphy and M. W. Davidson, Fundamentals of Light Microscopy and Electronic Imaging, 2$^{nd}$ Ed. John Wiley and Sons, Inc., Hoboken, N.J., 2016) or Schnatz et al. (T. Dockland, D. W. Hutmacher, M. Mah-Lee Ng, J.-T. Schantz in Manuals in Biomedical Research: Volume 2—Techniques in Microscopy for Biomedical Applications, World Scientific Publishing Co. Pte. Ltd., 2006). Explanation of common terms and methods in the preparation of (heavy) metal-complexes comprising one or more ligands may be found in Lawrance (G. A. Lawrance, Introduction to Coordination Chemistry, John Wiley and Sons Ltd., West Sussex, UK, 2010), Gispert (J. R. Gispert, Coordination Chemistry, Wiley-VCH Verlag GmbH & Co. KGaA, Weinheim, 2008), Soni and Soni (P. L. Soni and V. Soni in Coordination Chemistry: Metal Complexes, CRC Press—Taylor and Francis Group, Boca Raton, Fla., 2013) or Bhatt (Vasishta Bhatt, Essentials in coordination Chemistry—A simplified approach with 3D visuals, Academic Press—Elsevier, London, 2016). Explanation of common terms, methods and/or devices used in the computed tomography scanning (in particular X-ray absorption-based computed tomography scanning methods) of samples may be found in Haidekker (M. A. Haidekker in Medical Imaging Technologies—Computed Tomography, Springer Briefs in Physics, 2013, p. 37-53), Kachelrieß (M. Kachelrieß in Molecular Imaging I, Handbook of Experimental Pharmacology—Micro-CT, W. Semmler and M. Schwaiger (Eds.), Springer Verlag Berlin Heidelberg, 2008, Volume 185/1, p. 23-52.) or Stock (S. R. Stock in MircoComputed Tomography: Methodology and Applications, CRC Press—Taylor and Francis Group, Boca Raton, Fla., 2011).

The term "heavy metal" refers to metals having a density of more than 5 g/cm$^3$ and additionally includes the chemical elements strontium (Sr) and barium (Ba) as well as selenium (Se), rubidium (Rb), yttrium (Y) and caesium (Cs). Specifically, the term heavy metal refers to chemical elements selected from the group consisting of V (vanadium), Cr (chromium), Mn (manganese), Fe (iron), Co (cobalt), Ni (nickel), Cu (copper), Zn (zinc), Ga (gallium), Ge (germanium), As (arsenic), Se (selenium), Rb (rubidium), Sr (strontium), Y (yttrium), Zr (zirconium), Nb (niobium), Mo (molybdenum), Tc (technetium), Ru (ruthenium), Rh (rhodium), Pd (palladium), Ag (silver), Cd (cadmium), In (indium), Sn (tin), Sb (antimony), Te (tellurium), Cs (caesium), Ba (barium), La (lanthanum), Ce (cerium), Pr (praseodymium), Nd (neodymium), Pm (promethium), Sm (samarium), Eu, (europium), Gd (gadolinium), Tb (terbium), Dy (dysprosium), Ho (holmium), Er (erbium), Tm (thulium), Yb (ytterbium), Lu (lutetium), Hf (hafnium), Ta (tantalum), W (tungsten), Re (rhenium), Os (osmium), Ir (iridium), Pt (platinum), Au (gold), Hg (mercury), Tl (thallium), Pb (lead) and Bi (bismuth).

The terms "ligand" and "optional ligands" generally refers to an ion or molecule that binds to a central metal atom to form a coordination complex. The bonding with the metal generally involves formal donation of one or more of the ligand's electron pairs. Ligands are viewed as Lewis bases (although rare cases are known to involve Lewis acidic ligand).

The term "staining" as used herein refers to a procedure suitable for enhancing the contrast of images of a biological sample, in particular of images obtained by a computed tomography scanning method. Accordingly, staining of the biological sample does not necessarily require that the biological sample is colored after the staining procedure.

The term "water-based solution" or "aqueous solution" refers to solutions in which the main solvent is water. A given solvent is considered to be the "main solvent" if the solvent in question accounts for at least 55%, preferably at least 70%, more preferably at least 90%, particularly preferably at least 99%, and most preferably at least 99.9% of all solvents contained in the solution.

As used herein, the term "about" refers to ±10% of the indicated numerical value, and in particular to ±5% of the indicated numerical value. Whenever the term "about" is used, a specific reference to the exact numerical value indicated is also included. If the term "about" is used in connection with a parameter that is quantified in integers, the numbers corresponding to ±10% or ±5% of the indicated numerical value are to be rounded to the nearest integer. For example, in the context of integers the expression "about 25" refers to the range of 23 to 28, in particular the range of 24 to 26, and preferably refers to the specific value of 25.

If not indicated otherwise, concentrations given in percentages [%] refer to [weight/volume-%] in volume.

Heavy Metal Ion Complexes

The inventive complex comprises one or more heavy metal ion(s) M and one or more ligand(s) R, wherein at least one M is a heavy metal ion having an atomic number of 23 or higher and 83 or lower, and at least one R is hematein. Preferably, the inventive complex is represented by the following formula (I):

$$M_m R_n \qquad (I),$$

in which at least one M is a heavy metal ion having an atomic number of 23 or higher and 83 or lower, at least one R is hematein, and m and n are each independently 1, 2, 3, 4, 5, 6, 7, 8, 9, 10, 11 or 12.

It is to be noted that specific integers for m and n do not necessarily restrict the inventive heavy metal ion complex to exactly said composition of the complex but rather can also define the ratio of the heavy metal ion(s) M to the ligand R (i.e. m and n are integers said to be multiplicatively independent if their only common integer power is 1).

The inventive heavy metal ion complex, in addition to the one or more hematein ligands, optionally contains further ligand(s) (herein below sometimes referred to as "optional ligand(s)").

In accordance with the present invention, at least one M is an ion of a heavy metal having an atomic number of 23 or higher and 83 or lower, preferably 27 or higher and 83 or lower. Accordingly, in the heavy metal complexes of the present invention, the metal is present in different oxidation states, e.g. +1, +2, +3, etc. (also referred to as M(I), M(II), M(III), etc). Specifically, M is an ion of a chemical element selected from the group consisting of V (vanadium), Cr (chromium), Mn (manganese), Fe (iron), Co (cobalt), Ni (nickel), Cu (copper), Zn (zinc), Ga (gallium), Ge (germanium), As (arsenic), Se (selenium), Rb (rubidium), Sr (strontium), Y (yttrium), Zr (zirconium), Nb (niobium), Mo (molybdenum), Tc (technetium), Ru (ruthenium), Rh (rhodium), Pd (palladium), Ag (silver), Cd (cadmium), In (indium), Sn (tin), Sb (antimony), Te (tellurium), Cs (caesium), Ba (barium), La (lanthanum), Ce (cerium), Pr (praseodymium), Nd (neodymium), Pm (promethium), Sm (samarium), Eu (europium), Gd (gadolinium), Tb (terbium), Dy (dysprosium), Ho (holmium), Er (erbium), Tm (thulium), Yb (ytterbium), Lu (lutetium), Hf (hafnium), Ta (tantalum), W (tungsten), Re (rhenium), Os (osmium), Ir (iridium), Pt (platinum), Au (gold), Hg (mercury), Tl (thallium), Pb (lead) and Bi (bismuth), preferably M is an ion of a chemical element selected from the group consisting of Co, Ni, Cu, Zn, Ga, Ge, As, Zr, Nb, Mo, Tc, Ru, Rh, Pd, Ag, Cd, In, Sn, Sb, Te, Ba, La, Ce, Pr, Nd, Pm, Sm, Eu, Gd, Tb, Dy, Ho, Er, Tm, Yb, Lu, Hf, Ta, W, Re, Os, Ir, Pt, Au, Hg, Tl, Pb and Bi. More preferably, M is an ion of the chemical elements selected from the group consisting of Ag, Ba, Pb, Gd, Bi, Lu and La (i.e., $Ag^{1+}$, $Ba^{2+}$, $Pb^{2+}$, $Gd^{3+}$, $Bi^{3+}$, $Lu^{3+}$ and $La^{3+}$). Particular preferably, M is a heavy metal ion selected from the group consisting of $Ag^{1+}$, $Ba^{2+}$, $Pb^{2+}$, $Gd^{3+}$ and $Bi^{3+}$. Further preferable, M is a heavy metal ion selected from the group consisting of $Ag^{1+}$, $Ba^{2+}$, $Pb^{2+}$ and $Gd^{3+}$. Most preferably, M is $Ag^{1+}$ or $Ba^{2+}$ or $Pb^{2+}$ or $Gd^{3+}$ (in particular $Ba^{2+}$).

In other preferred embodiments M is an ion of a chemical element selected from the group consisting of Co, Ni, Cu, Zn, Ga, Ge, As, Zr, Mo, Tc, Ru, Rh, Pd, Cd, In, Sn, Sb, Te, Ba, Hf, Ta, W, Re, Os, Ir, Pt, Au, Hg and Tl.

The heavy metal ion M contained in the inventive heavy metal complexes, amongst others, provides properties resulting in X-ray attenuation, and therefore enhances the contrast of the imaged biological sample. Properties of interest are the atomic number, the density, the atomic mass and response to the applied energy. Moreover, it will be appreciated that the heavy metal M may comprise isotopes within one metal species, e.g. different isotopes of lead, etc.

Hematein (3,4,6a,10-Tetrahydroxy-6,7-dihydroindeno[2,1-c]chromen-9-one), having a structure represented by below Formula (II),

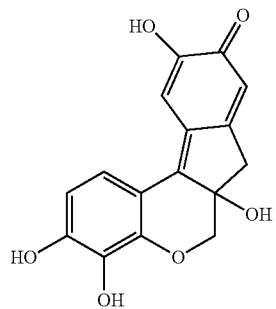

(II)

is an oxidized derivative of hematoxylin (7,11b-Dihydroindeno[2,1-c] chromene-3,4,6a,9,10(6H)-pentol), which is represented by below Formula (III)

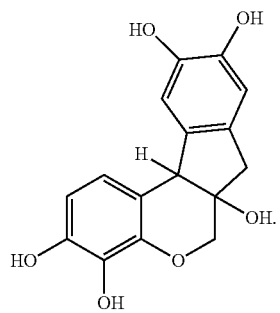

(III)

The aforementioned oxidation of hematoxylin can for instance be carried out by contacting a solution/suspension of hematein in absolute ethanol to air over a time period of several weeks (sometimes referred to as "ripening"). Alternatively, in order to speed up the oxidation process, oxidizing additives such as potassium iodate ($KIO_3$), sodium iodate ($NaIO_3$) or mercury oxide (HgO) can be added to a hematoxylin solution. Moreover, hematein and hematoxylin are both commercially available.

In general, the coordination number of a metal ion complex refers to the number of ligands (i.e. donor atoms) attached to the metal ion. For example, in the lead(II) complex of the present invention, the lead has a coordination number of at least two, for example it may be coordinated by or bonded to at least two groups such as the chelating moiety in hematein having the structure represented by Formula (IV)

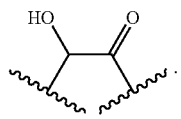

(IV)

In some embodiments, lead may have a higher coordination number, and it may for example additionally be coordinated by a neutral molecule such as $H_2O$. For instance, the lead(II) hematein complex may consist of lead(II) and two hematein ligands as shown in below Formula (V)

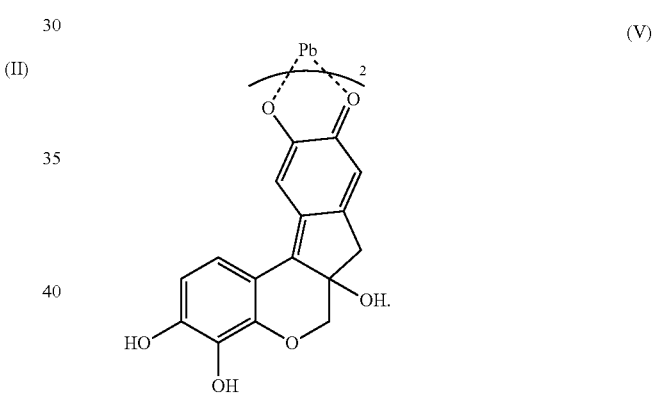

(V)

In above Formula (I), the number of hematein ligands is indicated by "n", which depends on several aspects such as the oxidation state of the heavy metal ion, the concentrations and equivalents used within the reaction mixture. The heavy metal ion M may be bonded to the oxygen donor atoms present in the chelating moiety of hematein, where the metal ion may be bonded through a structural motive having a structure represented by Formula (VI)

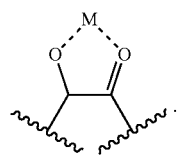

(VI)

Where the heavy metal hematein complex has a net overall charge (for example, not all coordination numbers of the metal centre are substituted by the ligand), the heavy metal hematein complex may be present in the form of a salt.

In principle, the counter ion may be any organic or inorganic moiety that stabilizes the charge on the parent complex.

The "optional ligand(s)" in the inventive heavy metal complexes are not particularly limited as long as a formation of the inventive complex with one or more hematein ligands is not hindered. Non-limiting examples of optional ligand(s) include $H_2O$, NO, hydrogen carbonate, hydrogen phosphate, carboxylates (e.g., formate, acetate, lactate, oxalate), chloride, etc.

Moreover, in some embodiments, the heavy metal complexes described herein may include solvates, hydrates, isomers, tautomers, racemates, stereoisomers, enantiomers or diastereoisomers of those complexes. Asymmetric centers may exist in the complexes disclosed herein. These centers can be designated by the symbols "R" or "S" depending on the configuration of substituents around the chiral carbon atom. It should be understood that the present invention encompasses all stereochemical isomeric forms, including diastereomeric, enantiomeric, and epimeric forms, as well as D-isomers and L-isomers, and mixtures thereof. Additionally, the complexes disclosed herein may exist as geometric isomers. The present invention includes all cis, trans, syn, anti, (E), and (Z) isomers as well as the appropriate mixtures thereof. Additionally, complexes may exist as tautomers, which are also included in the scope of the present invention. Moreover, the complexes disclosed herein may exist in polymorphic forms, which are also encompassed by the present invention.

In some embodiments, the heavy metal complexes may be present in the form of small particles, e.g. nanoparticles. Without wishing to be bound by any theory, it is considered that the diagnostic properties of the complexes may be improved where the complex is present in a form such that surface area is maximized, particularly where solubility of the complex is low, in order to maximize contact of the complex with the environment. Thus, in some embodiments, the inventive heavy metal complex is present in particulate form wherein the particles have a mean diameter (measured e.g. by laser diffraction) of less than 1000 µm, less than 500 µm, less than 200 µm, less than 100 µm, less than 50 µm, less than 20 µm, less than 10 µmm, less than 5 µm, less than 2 µm, or less than 1 µm. In some embodiments the metal hematein complex is present in particulate form wherein the particles have a mean diameter in the range of from 1000 µm to 500 µm, from 500 µm to 200 µm, from 200 µm to 100 µm, from 100 µm to 50 µm, from 50 µm to 20 µm, from 20 µm to 10 µm, from 10 µm to 5 µm, from 5 µm to 2 µm, or from 2 µm to 1 µm.

In further embodiments, the present invention provides a product, device, material, solution or composition comprising a heavy metal complex as defined above. In some embodiments the product, device, material, solution or composition is a medical product, device, material, solution or composition. In some embodiments the inventive heavy metal complex is distributed within the product, device, material, solution or composition. In some embodiments the product, device, material, solution or composition is a polymerizable and/or curable product, device, material, solution or composition.

Preparation of the Heavy Metal Ion Complexes

The inventive heavy metal ion complexes can be prepared by methods generally known to those skilled in the art. For instance, the following method can be used:

The exemplary method starts with the preparation of the two solutions (A) and (B). Solution (A) contains hematein in an appropriate solvent such as absolute ethanol. It is preferable that solution (A) has a hematein concentration near, or equal to, the maximum solubility of hematein. For instance, 10 g of the hematein precursor hematoxylin are dissolved in 100 mL of absolute ethanol. Solution (A) is kept stirring ensuring contact to air at room temperature for at least three to four weeks to allow for the oxidation (sometimes referred to as "ripening") of hematoxylin to the desired compound hematein. Alternatively, in order to speed up the oxidation process, oxidizing additives such as potassium iodate ($KIO_3$), sodium iodate ($NaIO_3$) or mercury oxide (HgO) can be added to a hematoxylin solution. The prepared solution (A) should be kept in the dark, in a closed, but well ventilated area and usually can be used for up to one year.

Solution (B) is prepared by solving the heavy metal ion source in a suitable solvent such as distilled water, alcohols (such as methanol and ethanol) and acetone. The one or more heavy metal ion(s) to be used in accordance with the method of the present invention are selected from the heavy metal ions listed above with regard to the inventive heavy metal ion complexes. Accordingly, the one or more heavy metal ion(s) derive from a chemical element selected from the group consisting of V (vanadium), Cr (chromium), Mn (manganese), Fe (iron), Co (cobalt), Ni (nickel), Cu (copper), Zn (zinc), Ga (gallium), Ge (germanium), As (arsenic), Se (selenium), Rb (rubidium), Sr (strontium), Y (yttrium), Zr (zirconium), Nb (niobium), Mo (molybdenum), Tc (technetium), Ru (ruthenium), Rh (rhodium), Pd (palladium), Ag (silver), Cd (cadmium), In (indium), Sn (tin), Sb (antimony), Te (tellurium), Cs (caesium), Ba (barium), La (lanthanum), Ce (cerium), Pr (praseodymium), Nd (neodymium), Pm (promethium), Sm (samarium), Eu (europium), Gd (gadolinium), Tb (terbium), Dy (dysprosium), Ho (holmium), Er (erbium), Tm (thulium), Yb (ytterbium), Lu (lutetium), Hf (hafnium), Ta (tantalum), W (tungsten), Re (rhenium), Os (osmium), Ir (iridium), Pt (platinum), Au (gold), Hg (mercury), Tl (thallium), Pb (lead) and Bi (bismuth). Preferably, the one or more heavy metal ion(s) derive from the group consisting of Co, Ni, Cu, Zn, Ga, Ge, As, Zr, Nb, Mo, Tc, Ru, Rh, Pd, Ag, Cd, In, Sn, Sb, Te, Ba, La, Ce, Pr, Nd, Pm, Sm, Eu, Gd, Tb, Dy, Ho, Er, Tm, Yb, Lu, Hf, Ta, W, Re, Os, Ir, Pt, Au, Hg, Tl, Pb and Bi. More preferably, the one or more heavy metal ion(s) derive from the group consisting of Ag, Ba, Pb, Gd, Bi, Lu and La (i.e., $Ag^{1+}$, $Ba^{2+}$, $Pb^{2+}$, $Gd^{3+}$, $Bi^{3+}$, $Lu^{3+}$ and $La^{3+}$). Particularly preferable, the one or more heavy metal ion(s) derive from the group consisting of $Ag^{1+}$, $Ba^{2+}$, $Pb^{2+}$, $Gd^{3+}$ and $Bi^{3+}$. Further preferably, the one or more heavy metal ion(s) derive from the group consisting of $Ag^{1+}$, $Ba^{2+}$, $Pb^{2+}$ and $Gd^{3+}$, most preferably $Ag^{1+}$ or $Ba^{2+}$ or $Pb^{2+}$ or $Gd^{3+}$ Suitable salts of the above heavy metals are well known in the art and are commercially available. The heavy metal ion source is usually a salt of the respective heavy metal(s) which is/are sufficiently soluble in the respective solvent. Suitable salts of the heavy metal are well known in the art and are commercially available. The maximum concentration of the one or more heavy metal ion(s) in the solution(s) (B) of course depends on the solubility of the respective heavy metal ion salt used to prepare the one or more solution(s) (B). In general, it can be beneficial to use higher concentrated solutions. Preferably, the amount of the respective heavy metal ion(s) is equimolar to solution (A) or twice as concentrated (compensating for a possible over-oxidation of hematein to oxyhematein). The prepared solution B should be kept in the dark, in a closed, but well ventilated area and usually can be used for up to one year.

The inventive complex is prepared by mixing the two solutions to obtain a solution (AB). Preferably, the two solutions are mixed in a 1:1 ratio. More preferably, mixing is carried out immediately before staining of the biological sample. Complex formation is usually indicated by a color change of the solution after mixing. Moreover, the color of the inventive heavy metal complex can depend on the nature of the metal ion and e.g. on the solvent utilized. For instance, in the case of lead(II) the final complex in an ethanol-water-mixture has a dark blue color. For use in the inventive ex vivo method, the complex obtained by the afore-mentioned method can be directly used for staining of the biological sample.

As mentioned above, the inventive heavy metal ion complexes are in particular useful as contrast agents for a computed tomography scanning of biological samples. The term "computed tomography", in brief "CT", includes all computed tomography scanning methods available to those skilled in the art. Non limiting examples of CT scanning methods are X-ray absorption-based CT, X-ray propagation phase-contrast CT and X-ray grating interferometry phase-contrast CT. Preferred CT scanning methods are X-ray absorption-based scanning methods. In general, a CT scan makes use of computer-processed combinations of many X-ray images taken from different angles to produce cross-sectional (tomographic) images (virtual "slices") of specific areas of a scanned sample. Digital geometry processing is used to generate a three-dimensional image of the inside of the sample from a large series of two-dimensional radiographic images taken around a single axis of rotation. Medical imaging is the most common application of X-ray CT. Non-limiting examples of X-ray absorption-based scanning methods are attenuation-based imaging, dual-energy imaging, K-edge imaging and spectral decomposition. More preferred CT scanning methods are X-ray absorption-based Micro-Computed Tomography ($\mu$CT) and Nano-Computed Tomography (NanoCT). The prefix micro-(symbol: $\mu$) is used in the term "Micro-Computed Tomography" to indicate that the pixel sizes of the cross-sections are in the micrometer range. These pixel sizes have also resulted in terms such as high-resolution x-ray tomography and X-ray microtomography. The prefix nano- is used in the term "Nano-Computed Tomography" to indicate that the pixel sizes of the cross-sections are in the nanometer range. Suitable devices for carrying out the aforementioned CT scanning methods are commercially available. For instance, non-limiting examples of commercially available $\mu$CT devices are V|tome|X (designed and developed by GE) and XRadia (designed and developed by Zeiss).

In addition to the above-described use as an ex vivo contrast agent for a computed tomography scanning of a biological sample, the inventive complexes may have a plethora of further applications. Non-limiting examples thereof are the use as diagnostic additives for coating surfaces of products, in a curable composition (e.g., an adhesive compositions), in a coating composition for coating the surface of an object (e.g. a composition comprising a film former/binder, the inventive complex, and optionally other components such as diluents(s), pigment(s), and/or filler(s)), and in a monomer composition comprising a polymerizable monomer which is intended for polymerisation to produce a polymerised product and in a polymeric material (e.g., the inventive complex may be dispersed as a separate component within the bulk of the polymeric material; alternatively, the inventive complex may be present in the polymeric material as an integral part of the polymer (i.e. covalently bound to the polymer)).

Further, a product may be coated with a diagnostic surface coating comprising the inventive complex. For example, the exterior of a product may be covered by spraying or coating with a composition comprising the inventive complex. In some embodiments, for example where the inventive complex has low solubility, the composition may take the form of a suspension composition comprising the inventive complex suspended in a liquid carrier.

The amount of the inventive complex used in products, compositions and the like will depend on the nature of the material and the intended application. In some embodiments, the inventive complex is present in an amount of up to 25, up to 20, up to 15, up to 10, up to 5, up to 2, up to 1, up to 0.5, up to 0.2, up to 0.1, up to 0.05, up to 0.02, up to 0.01, up to 0.005, up to 0.002, or up to 0.001% by weight of the product, material, device or composition which comprises the inventive complex.

The diagnostic properties of the inventive complexes make them particularly suitable for use in the hospital/medical environment. Accordingly, in some embodiments the product, device, material, solution or composition comprising the inventive complex is a medical product, device, material, solution or composition, such as a wound dressing, a suture, a surgical implement or a medical implant. For example sutures or stitches (e.g. stitches formed of polymers having glycolic acid and/or lactic acid monomer units, such as polygalactin 910) may be coated with a coating composition comprising the inventive complex, or the stitches formed from monomer compositions containing the inventive complex. Surgical equipment and implements, and medical implants such as dental implants, stents and components used in joint arthroplasty, may be coated with a coating composition comprising the inventive complex or, where appropriate, formed of a composition comprising the inventive complex. The inventive complex may also or alternatively find use in wound dressings. For example the product may be a wound dressing comprising a woven material made of synthetic and/or natural polymer (e.g. polyurethane, polyester, cotton) coated or impregnated with a composition comprising the inventive complex, or, in the case of a synthetic polymer, formed of a monomer composition containing the inventive complex. The medical product, device, composition or material comprising the inventive complex may also be a curable medical adhesive (e.g. a cyanoacrylate composition), a bone or dental cement (e.g. methyl methacrylate/polymethyl methacrylate compositions), a dental primer or dental adhesive. Medical consumables (where diagnostic properties are desirable) may also comprise the inventive complex.

As discussed above, the inventive complex may be used to impart diagnostic properties to a variety of medical products. For example wound dressings coated or impregnated with the inventive complex, in particular with the inventive complex comprising silver ions, may be applied to the skin of a patient, or the inventive complex may be present in a bone cement composition to visualize the attachment to the human body following joint replacement surgery.

Moreover, the inventive complex may also find use in applications outside the medical environment. For example, the inventive complex may find use in products, devices, materials or compositions used in building construction, renovation and/or maintenance. Examples of compositions which may comprise the inventive complex include curable and/or polymerizable compositions, such as coating compositions (e.g. lacquer compositions, varnish compositions, or paint compositions comprising a binder or film former, and optionally other components such as pigment(s) and/or diluents(s)), adhesive or sealant compositions (e.g. a silicone or polyurethane sealant composition), cement compositions (e.g. a Portland-type cement composition comprising calcium silicates), concrete (e.g. compositions comprising cement, aggregates and water), or grout, mortar or stucco compositions (e.g. compositions comprising water, cement and sand).

Ex Vivo Method for Investigating a Biological Sample

In a first aspect, the present invention relates to an ex vivo method for investigating a biological sample comprising: (a1) staining the biological sample with a solution (AB) comprising one or more complex(es) as defined above.

In a second aspect (herein below sometimes referred to as "in situ staining"), the present invention relates to an ex vivo method for investigating a biological sample comprising: (a2) staining the biological sample with (i) a solution (A) comprising hematein, and (ii) one or more solution(s) (B) comprising one or more heavy metal ion(s) as defined above, wherein the biological sample is contacted with solution (A) separately from the one or more solution(s) (B). Without wishing to be bound by any theory, the afore-mentioned in situ staining facilitates the formation of the heavy metal ion-ligand complex directly in the biological sample to be investigated, i.e. in situ.

In both aspects of the inventive ex vivo method, the biological sample is subjected to a computed tomography scanning method after staining (and is therefore "investigated"). Herein below, the inventive ex vivo method is explained in more detail. If not indicated otherwise, these explanations equally apply to the first as well as the second aspect of the inventive ex vivo method.

The term "biological sample" refers to any material of biological origin to be analyzed. Non-limiting examples of biological samples are organs and tissues, preferably tissues, more preferably soft tissues, most preferably human soft tissues. In biology, tissue is a cellular organizational level intermediate between cells and a complete organ. A tissue is an ensemble of similar cells from the same origin that together carry out a specific function. Organs are then formed by the functional grouping together of multiple tissues. It is to be understood that the biological sample to be analyzed can also be part of an organ or tissue, or can be an aggregation of organs and/or tissues.

The term "soft tissue" refers to tissues that connect, support, or surround other structures and organs of the body, not being hard tissue such as bone. Non-limiting examples of soft tissue are tendons, ligaments, fascia, skin, fibrous tissues, fat, and synovial membranes (which are connective tissue), and muscles, nerves and blood vessels (which are not connective tissue). Preferred soft tissues samples used in the present invention originate from lung, kidney, liver, brain, spleen, heart and cartilage.

The biological sample originates from an animal such as birds and mammals, wherein mammals are preferred. The mammal may be, e.g., a rodent (such as, e.g., a guinea pig, a hamster, a rat or a mouse), a canine (such as, e.g., a dog), a feline (such as, e.g., a cat), a porcine (such as, e.g., a pig), an equine (such as, e.g., a horse), a primate, a simian (such as, e.g., a monkey or an ape), a monkey (such as, e.g., a marmoset or a baboon), an ape (such as, e.g., a gorilla, a chimpanzee, an orang-utan or a gibbon), or a human. It is envisaged that the biological sample is also obtained from non-human mammals, which are economically, agronomically or scientifically important. Scientifically important mammals include, e.g., mice, rats and rabbits. Non-limiting examples of agronomically important mammals are sheep, cattle and pigs. Economically important mammals include, e.g., cats and dogs. Most preferably, the biological sample is obtained from a human.

The biological sample used in accordance with the invention is obtainable by suitable methods for obtaining biological samples generally known in the art. For example, the biological sample can be obtained by excision (cutting out), puncture (also called centesis) followed by aspiration, and scraping or swiping.

The biological sample used in the staining method according to the present invention can be used directly (e.g., fresh or frozen), or can be manipulated prior to staining. Suitable manipulation procedures for biological samples are well known in the art, and non-limiting example procedures are for instance described in Mulisch and Welsch (M. Mulisch and U. Welsch, Romeis Mikroskopische Technik, 19th Ed. Springer Spektrum Akademischer Verlag, Heidelberg, 2010) and Lang (G. Lang, Histotechnik: Praxislehrbuch für die Biomedizinische Analytik, 2nd Ed. Springer-Verlag Wien, 2013). Preferably, the biological sample is subjected to chemical fixation by means of chemical fixatives prior to staining. Chemical fixatives are, amongst others, used to preserve the biological sample from degradation, and to maintain the structure of the cell and of sub-cellular components. Examples of chemical fixatives include, but are not limited to, water-based solutions of formaldehyde or glutaraldehyde (or mixtures thereof), methanol, ethanol and acetone. A preferred chemical fixative according to the present invention is a water-based formaldehyde solution, more preferably a formaldehyde solution in Dulbecco's phosphate buffered saline (DPBS) or a formaldehyde solution in phosphate buffered saline, particularly preferable is a formaldehyde solution in Dulbecco's phosphate buffered saline, most preferably a formaldehyde solution in Dulbecco's phosphate buffered saline (DPBS) without calcium and magnesium. The constituents of Dulbecco's phosphate buffered saline can be taken from VWR—Amresco LifeScience (137 mM sodium chloride, 2.7 mM potassium chloride and 10 mM phosphate buffer, without calcium and magnesium).

The concentration of the aldehyde-based chemical fixative (e.g. formaldehyde) in the water-based solution can vary considerably but is usually in the range of about 0.5 to about 15%, preferably about 0.8 to about 10%, more preferably about 1 to about 5%, particularly preferably about 2 to about 4%, and most preferably about 4%. Preferably, an acid (e.g., glacial acetic acid) is additionally present in the water-based formaldehyde solution since this may improve the diagnostic value of the inventive staining method. Examples of suitable acids are glacial acetic acid and citric acid. Preferably, glacial acetic acid is used. The concentration of the acid in the chemical fixative is usually in the range of about 0.5 to about 15%, preferably about 1 to about 10%, more preferably about 2 to about 6%, particularly preferably about 3 to about 5%, and most preferably about 5%.

The time period of the chemical fixation procedure can vary considerably, but is usually in the range of about 3 to about 120 hours, preferably about 6 to about 96 hours, more preferably about 9 to about 84 hours, particularly preferably about 12 to about 72 hours, and most preferably about 18 to about 48 hours. After the fixation period, the biological sample is preferably washed 1 or more times, preferably 2 or more times, more preferably 3 or more times, particularly preferably 4 or more times, and most preferably 5 or more times with a suitable water-based solution. Preferably, the washing is carried out with a suitable buffer (e.g., Dulbecco's phosphate buffered saline or phosphate buffered saline). Subsequently, the biological sample can be subjected directly to staining, can be stored for a desired amount of time (preferably under cooling) prior to staining, or can be further manipulated prior to staining.

Subject to the specific nature of the biological sample (e.g., biological origin, sample size, etc.), the skilled person can adopt the characteristics of the fixation protocol (such as nature and concentration of the chemical fixative, fixation time, temperature, etc.) in a suitable manner In the first aspect of the inventive ex vivo method, the method comprises a step of staining the biological sample with a solution (AB) comprising one or more complex(es) as defined above. An exemplary method for the preparation of solution (AB) has already been described above. Preferably, the concentration of complex-bound hematein in solution (AB) is in the range of about 150 to about 500 mM, or about 200 to about 450 mM. More preferably, the concentration of complex-bound hematein in solution (AB) is in the range of about 250 to about 400 mM. Particularly preferably, the concentration of complex-bound hematein in solution (AB) is in the range of about 300 to about 400 mM. Most preferably, the concentration of complex-bound hematein in solution (AB) is in the range of about 300 to about 350 mM.

For the staining of the biological sample according to the first aspect of the inventive ex vivo method, the biological sample is brought into contact with the solution (AB), e.g. by submerging it in solution (AB). The time of contacting the biological sample with solution (AB) is the incubation time (staining time). The incubation time (staining time) between solution (AB) and the biological sample is not particularly limited and for instance depends on the specific nature of the biological sample (e.g., biological origin, sample size, etc.). The incubation time of the biological sample with solution (AB) (staining time) is preferably a time period of 12 hours or more, more preferably of 24 hours or more. Particular preferably, the time period is 48 hours or more. Further preferably, the time period is 96 hours or more. Most preferably, the time period is 168 hours or more.

In the second aspect of the inventive ex vivo method (in situ staining), the biological sample is contacted with solution (A) separately from the one or more solution(s) (B). Exemplary methods for the preparation of solutions (A) and the one or more solution(s) (B) has already been described above when describing an exemplary method for the preparation of the heavy metal ion complex. It is reiterated that the one or more heavy metal ion(s) to be used in accordance with the method of the present invention are selected from the heavy metal ions listed above with regard to the inventive heavy metal ion complexes.

Preferably, the concentration of hematein in solution (A) is in the range of about 150 to about 500 mM, more preferably about 200 to about 450 mM. Particular preferably, the concentration of hematein in solution (A) is in the range of about 250 to about 400 mM. Further preferably, the concentration of hematein in solution (A) is in the range of about 300 to about 400 mM. Most preferably, the concentration of hematein in solution (A) is in the range of about 300 to about 350 mM. The maximum concentration of the one or more heavy metal ion(s) in the solution(s) (B) of course depends on the solubility of the respective heavy metal ion salt used to prepare the one or more solution(s) (B). In general, it can be preferable to use higher concentrated solutions.

For the staining of the biological sample according to the second aspect of the inventive ex vivo method, the biological sample is contacted with solution (A) separately from the one or more solution(s) (B), e.g. by submerging it in the respective solutions separately. The time of contacting the biological sample with solution (A) or the one or more solution(s) (B) is the incubation time (staining time) of the biological sample in the respective solution. The incubation time (staining time) of solution (A) and the incubation time (staining time) of the one or more solution(s) (B) are preferably 12 hours or more, more preferably 24 hours or more. Particular preferably, the time period is 48 hours or more. Further preferably, the time period is 96 hours or more. Most preferably, the time period is 168 hours or more. The incubation time (staining time) of solution (A) or the one or more solution(s) (B) are independent from each other, i.e., can be the same or different.

Moreover, the biological sample is preferably washed 1 or more times, more preferably 2 or more times, particular preferably 3 or more times, further preferably 4 or more times, and most preferably 5 or more times with a suitable water-based solution between the separate staining steps. Preferably, the washing is carried out with a suitable buffer (e.g., Dulbecco's phosphate buffered saline or phosphate buffered saline).

The present inventors surprisingly found that an in situ staining of the biological sample can result in particularly favorable staining results in terms of homogeneity throughout the biological sample and/or CT contrast enhancement. As regards contrast enhancement, it has been found that the quality of the CT results can be further improved if the biological sample is contacted with solution (A) before the biological sample is contacted with the one or more solution(s) (B). Further improvements can be achieved if the main solvent of solution (A) is different to the main solvent of the one or more solution(s) (B). Most preferably, the main solvent of solutions (A) is ethanol, and the main solvent of the one or more solution(s) (B) is a water-based solution.

Additionally, it has been found that in situ staining allows for the use of easy reducible heavy metals (e.g., $Ag^+$) in hematein-based staining. Specifically, it has been found that a solution comprising both an easy reducible heavy metal ion source (e.g., $AgNO_3$) and hematein resulted in the precipitation of the elemental heavy metal (e.g., Ag). The elemental heavy metal can "clog" the pores of the biological sample thereby making it difficult to obtain homogenous staining results. Without wishing to be bound by any theory, it is believed that the presence of an easy reducibly heavy metal ion source might result in an over-oxidation of hematein to oxyhematein, which can further compromise the staining result.

As mentioned before, the inventive ex vivo method (first as well as the second aspect) are compatible with conventional histological methods. This means that the contrast enhancement achieved by the inventive ex vivo method with regard to CT does not preclude a further investigation of regions of interest with conventional histological methods, if desired. Furthermore, in preferred embodiments, the inventive ex vivo method comprises, in addition to staining step (a1) or staining step (a2) an additional step of staining with an additional staining agent. Preferably, the additional staining agent is a xanthene derivative as described herein below, more preferably the additional staining agent is selected from the group consisting of eosin Y and erythrosine B. In principle, the additional step of staining with an additional staining agent can be carried out before or after the staining step (a1) or staining step (a2). However, it is preferably to carry out the additional staining after the staining step (a1) or staining step (a2) in terms of staining quality. In case of in situ staining (in particular in case of lead(II) ion as a heavy metal), it is more preferable that the additional step of staining with an additional staining agent is carried out after staining steps (a2)(i) and staining step (a2)(ii) have been both completed. Particularly preferably, the in situ staining (in particular in case of lead(II) ion as a heavy metal) is carried out in the order of 1) staining step (a2)(ii), 2) staining step (a2)(i) and 3) staining with the additional staining agent (in particular eosin Y).

The xanthene derivatives which can be used as additional staining agent are represented by the Chemical Formula (I) below:

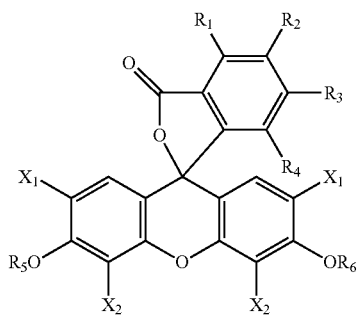

(I)

wherein
$X_1$ is each independently $NO_2$, halogen or H,
$X_2$ is each independently Halogen or H,
$R_1$, $R_2$, $R_3$ and $R_4$ are each independently H, halogen (independently selected from the group consisting of Cl, Br and I) or a water solubility enhancing group selected from OH, $NH_2$, SH, $NO_2$, $SO_3H$, $SO_4H_2$, $PO_3H_2$ diol and polyols such as polyethyleneglycols, and $R_5$ and $R_6$ are each independently H or a water solubility enhancing group selected from $NH_2$, SH, $NO_2$, $SO_3H$, $SO_4H_2$, $PO_3H_2$ diol and polyols such as polyethyleneglycols.

Preferred examples of the xanthene derivatives used in the present invention are mono-, di-, tri- and tetrachlorofluoresceines; mono-, di-, tri-, and tetrabromofluoresceines; Solvent Red 72; mono-, di, tri- and tetraiodofluoresceines; eosin B; eosin Y; ethyleosin; erythrosin B; phloxine B and Rose bengal (4,5,6,7-tetrachloro-2',4',5',7'-tetraiodofluorescein). The following compounds are preferred:

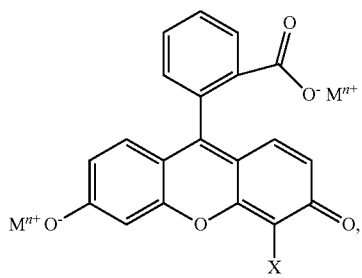

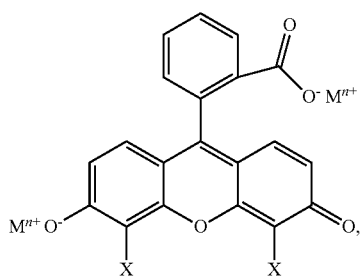

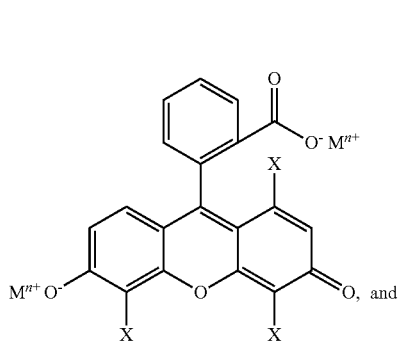

, and

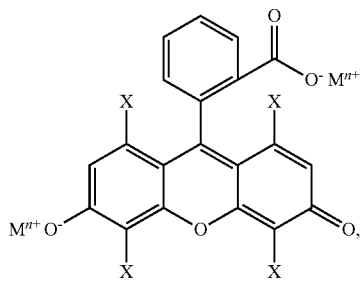

wherein M is metal ion (such as $Na^+$ or $Ba^{2+}$) which can be present in different oxidation states (e.g. +1, +2 etc) and X is a halogen (independently selected from the group consisting of Cl, Br and I). More preferred are the compounds shown below:

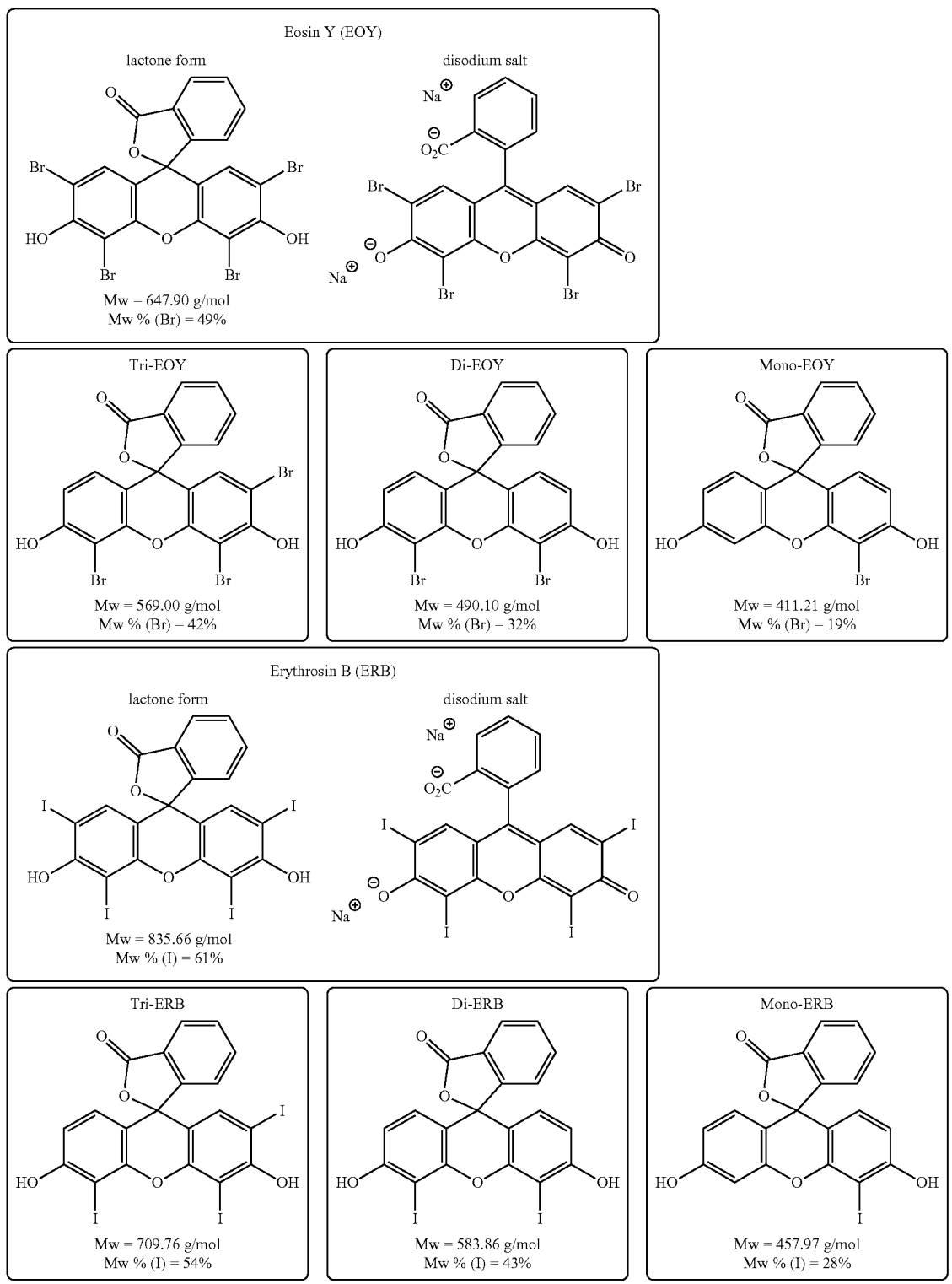

Particular preferred are mono-, di-, tribromofluorescein; mono-, di, triiodofluorescein; eosin B; eosin Y and erythrosin B. Most preferred are eosin Y and erythrosin B.

The afore-mentioned xanthene derivatives can be prepared by methods described herein and/or standard synthesis procedures known to the person skilled in the art. For example, the dibromo eosin derivative was synthesized as follows: A Schlenk flask was charged with 1.00 g of fluorescein (lactone form 0.1 M), which was dissolved in methanol and cooled to 0° C. N-bromo succinimide or N-iodo succinimide was added in corresponding equivalents of 1.1, 2.2 and 3.3 equivalents to the solution. The resulting suspension was stirred vigorously for 2 hours at room temperature. The solvent was removed in vacuum and the residue was taken up in an aqueous sodium hydroxide solution (1 M, 10 ml) and stirred for 30 min. The deep red solution was treated with a 1 M aqueous hydrogen chloride solution until no further precipitation was observed. The remaining reaction mixture was stirred for another 3 hours. The precipitate is filtered off and purified with MPLC (medium pressure liquid chromatography: stationary phase: reversed phase C18 column, 12 g dry weight, column from Revelis; mobile phase: acetonitrile/water gradient: 35/65 for 0-5 min; 40/60 for 5-20 min and 100/0 for 20-45 min) to yield the brominated derivatives of eosin or the iodinated derivatives of erythrosine B.

As a further example, the dibromo metal eosin derivative, e.g. barium was synthesized as follows: To a suspension of an eosin Y/erythrosine B derivative (lactone form, 1.00 equivalent) in 250 ml of water (milli-Q quality) was added a heavy metal salt (M=$Pb^{2+}$, $Cu^{2+}$, $Ba^{2+}$ with 1.00 equivalent and $Na^+$ with 2 equivalents). The reaction mixture was stirred at room temperature and after 12 hours a deep red suspension was observed. The reaction mixture was filtered, and the solvents were removed in vacuum. The remaining residue was dried in vacuum for 12 hours to yield a crystalline coloured (from orange over deep red to purple.)

Moreover, some of the aforementioned xanthene derivatives such as eosin Y and erythrosin B are commercially available and can be used for the preparation of the heavy metal ligand complex. Eosin Y and erythrosin B are both commercially available in the form of the respective sodium salts as well as in the form of the closed lactones, which are shown in Chemical Formula (II) below:

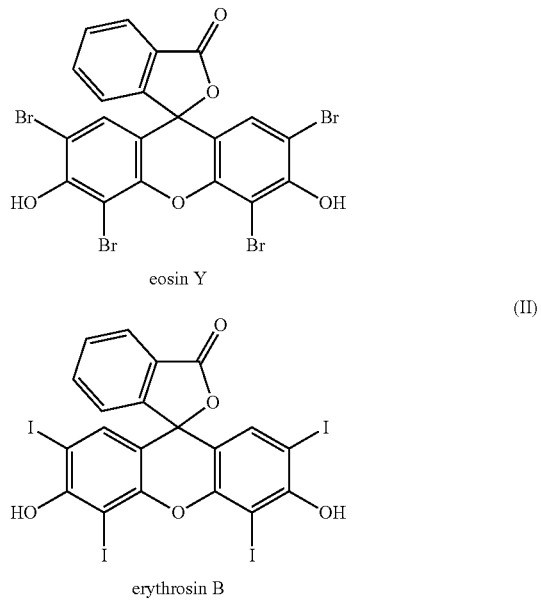

(II)

The additional staining can be carried out before subjecting the stained biological sample to a computed tomography scanning method, or thereafter. It is noted that an additional staining with conventional stains (e.g., eosin Y and/or erythrosine B; i.e., stains with affinity for the cytoplasm) can be advantageous in terms of a further investigation with conventional histological methods. It is, however, also noted that the additional staining with conventional stains such as eosin Y and erythrosine B can also be carried out with the three-dimensional biological sample, i.e., it is not obligatory that the additional staining is carried out with sliced tissue sections used in conventional histological investigations.

In other embodiments, the inventive ex vivo method does not comprise, in addition to staining step (a1) or staining step (a2), an additional step of staining with an additional staining agent.

The inventive ex vivo method comprises a step of subjecting the stained biological sample to a CT scanning method. Suitable CT scanning methods/devices have already been described above. For instance, the biological sample may be imaged in a commercially available X-ray μCT setup, e.g. the V|tome|X.

In the step of subjecting the stained biological sample to a CT scanning method, for instance, the biological sample is placed in an appropriate container that holds the sample in such a fashion that the biological sample is not subjected to moving (cf., FIG. 6). Moreover, for instance, the following parameters may be used to acquire the CT of the stained biological sample of the present invention:

(i) V|tome|X: U=30-60 kV, I=100-250 μA, average=3, skip=1, exposure time depended on nature of CA used, pixel size depended on sample size, overall scan time depended on number of projections for tomography.

(ii) XRadia: U=30-60 kV, P=1.8-4.5 W, average=3, skip=1, exposure time depended on nature of CA used, pixel size depended on sample size and objective chosen for measurement, overall scan time depended on number of projections for tomography.

Use of the Inventive Heavy Metal Ion Complexes as a Contrast Agent for CT Scanning of a Biological Sample Moreover, the present invention relates to the use of the inventive heavy metal complexes as a contrast agent for a CT scanning of a biological sample. The above explanations with regard to the heavy metal complexes, suitable CT scanning methods/devices and the potential biological samples to be investigated equally apply, mutatis mutandis, to the use of the disclosed heavy metal complexes.

It is to be understood that the present invention specifically relates to each and every combination of features and embodiments described herein, including any combination of general and/or preferred features/embodiments. In particular, the invention specifically relates to all combinations of preferred features (including all degrees of preference) of the methods and products provided herein. Moreover, those skilled in the art will appreciate that the disclosure herein is susceptible to variations and modifications other than those specifically described. It is to be understood that the invention includes all obvious variations and modifications of said disclosure.

In this specification, a number of documents including scientific literature are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference. Moreover, it will be understood that, although a number of documents are referred to herein, this reference does not—in itself—constitute an admission that any of these documents forms part of the common general knowledge of the skilled person.

The invention will now be described by reference to the following examples which are merely illustrative and are not to be construed as a limitation of the scope of the present invention.

EXAMPLES

Example 1

Figure 1:
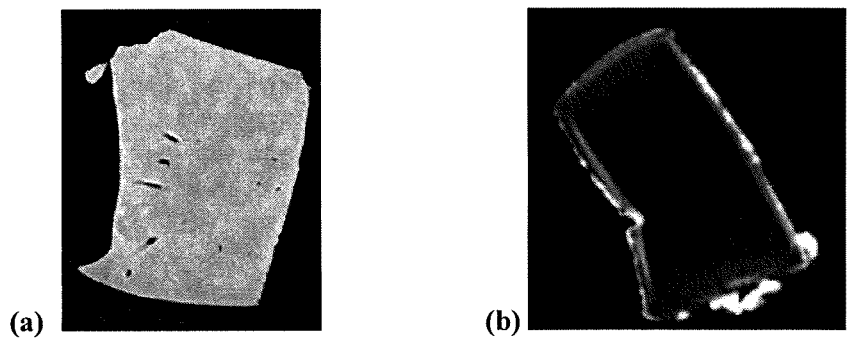
FIG. 1: (a) Mouse liver sample stained with the "in situ" staining method applying the silver(I) nitrate solution (332 mM) for 168 hours and hematein solution (332 mM) for 168 hours. (b) Mouse liver sample stained for 72 hours with the preformed silver(I) hematein complex (working solution A (332 mM) and B (332 mM) were mixed before in a 1:1 ratio).

An in 4 vol/vol-% formaldehyde (FA, derived from a 37% acid free FA solution stabilized with ca. 10% methanol from Carl Roth) fixated mouse liver sample was placed in a sample container with a flat bottom holding 2 ml of working solution (B) containing 332 mM silver(I) nitrate ($AgNO_3$) in distilled water. The soft tissue sample was kept for 168 hours in the staining solution, which was placed on a horizontal rocking plate and kept in the dark. The soft tissue sample was removed with tweezers after 168 hours of staining and the residual staining solution was carefully removed with a cellulose tissue paper without pressing or modifying the soft tissue sample in any way. Then the soft tissue sample was placed in a new sample container with a flat bottom holding 2 ml of working solution (A) containing 332 mM of hematein in absolute ethanol. The tissue sample was kept for 168 hours in the staining solution, which was placed on a horizontal rocking plate and kept in the dark. The tissue sample was removed with tweezers after 168 hours of staining and the residual staining solution was carefully removed with a cellulose tissue paper without pressing or modifying the soft tissue sample in any way. The stained tissue sample was placed above 70 vol/vol-% ethanol vapor. The soft tissue sample was measured at a micro-computed tomography setup, the phoenix v|tome|x s 240 CT scanner from GE with the following parameters: U=40 kV, I=280 µA, P=11.2 W, average=3, skip=1, t=1 s, projections=1001, resolution=24.755 µm and an overall scan time of 67 min. A tomographic slice is shown in FIG. 1(a).

An in a mixture of 1 vol/vol-% formaldehyde (FA, derived from a 37% acid free FA solution stabilized with ca. 10% methanol from Carl Roth) and 2.5 vol/vol-% glutaraldehyde (GA, derived from a 25% GA solution from Sigma Aldrich) fixated mouse liver sample was placed in a sample container with a flat bottom holding 2 ml of a staining solution containing the hematein silver(I) complex (a working solution (A) containing 332 mM of hematein in absolute ethanol and a working solution (B) containing 332 mM of $AgNO_3$ were mixed prior to adding the soft tissue sample in a ratio of 1:1). Immediately after contacting working solution (A) with working solution (B), the formation of a silver mirror was observed at the sample container walls indicating the reduction of the silver(I) ion to the silver metal. The tissue sample was kept for 72 hours in the staining solution, which was placed on a horizontal rocking plate and kept in the dark. The tissue sample was removed with tweezers after 72 hours of staining and the residual staining solution was carefully removed with a cellulose tissue paper without pressing or modifying the soft tissue sample in any way. The stained tissue sample was placed above 70 vol/vol-% ethanol vapor. The tissue sample was measured at a micro-computed tomography setup, the phoenix v|tome|x s 240 CT scanner from GE with the following parameters: U=60 kV, I=240 µA, P=14.4 W, average=3, skip=1, t=1 s, projections=1001, resolution=7,395 µm and an overall scan time of 67 min. A tomographic slice is shown in FIG. 1(b).

Example 2

Figure 2:
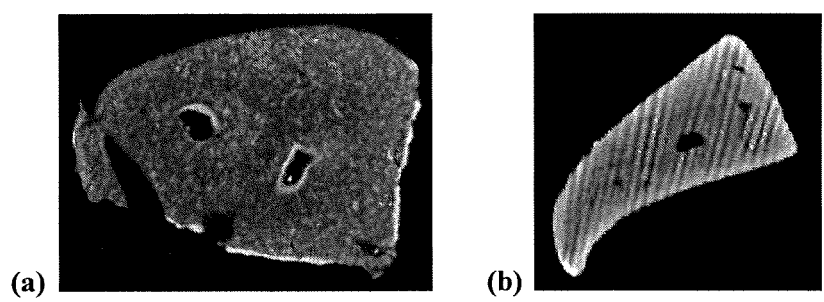
FIG. 2: (a) Mouse liver sample stained with the "in situ" staining method applying lead(II) acetate solution (664 mM) for 72 hours and hematein solution (332 mM) for 72 hours. (b) Mouse liver sample stained for 72 hours with the preformed hematein lead(II) complex (working solution A (332 mM) and B (664 mM) were mixed before in a 1:1 ratio).

An in 1 vol/vol-% formaldehyde (FA, derived from a 37% acid free FA solution stabilized with ca. 10% methanol from Carl Roth) fixated mouse liver sample was placed in a sample container with a flat bottom holding 2 ml of the working solution (B) containing 664 mM lead(II) acetate ($Pb(CH_3COO)_2$) in distilled water and one drop of glacial acetic acid. The soft tissue sample was kept for 72 hours in the staining solution, which was placed on a horizontal rocking plate. Then working solution (A) containing 332 mM of hematein in absolute ethanol was added to the same sample container resulting in an immediate color change to dark blue, which indicated complex formation. The soft tissue sample was kept for further 72 hours on a horizontal rocking plate and kept in the dark. After staining, the soft tissue sample was removed with tweezers and the residual staining solution was carefully removed with a cellulose tissue paper without pressing or modifying the soft tissue sample in any way. The stained tissue sample was washed with distilled water (3×6 ml) for 5 minutes (in total 3 washes) and placed above 70 vol/vol-% ethanol vapor. The soft tissue sample was measured at a micro-computed tomography (µCT) setup, the phoenix v|tome|x s 240 CT scanner from GE with the following parameters: U=40 kV, I=210 µA, P=8.4 W, time=2 s, average=3, skip=1, projections=1001, resolution=8.799 µm and an overall measurement time of 134 min. A tomographic slice is shown in FIG. 2(a). Moreover, the in situ formation of the lead(II) hematein complex as a result from the two step staining protocol is also evidenced by the histological investigations shown in FIGS. 7 and 8.

An in 1 vol/vol-% formaldehyde (FA, derived from a 37% acid free FA solution stabilized with ca. 10% methanol from Carl Roth) fixated mouse liver sample was placed in a sample container with a flat bottom holding 2 ml of a staining solution containing the hematein lead(II) complex (a working solution (A) containing 332 mM of hematein in absolute ethanol and a working solution (B) containing 664 mM of $Pb(CH_3COO)_2$ were mixed prior to adding the soft tissue sample in a ratio of 1:1). The tissue sample was kept for 72 hours in the staining solution, which was placed on a horizontal rocking plate and kept in the dark. The tissue sample was removed with tweezers after 72 hours of staining and the residual staining solution was carefully removed with a cellulose tissue paper without pressing or modifying the soft tissue sample in any way. The stained tissue sample was placed above 70 vol/vol-% ethanol vapor. The tissue sample was measured at a micro-computed tomography setup, the phoenix v|tome|x s 240 CT scanner from GE with the following parameters: U=60 kV, I=240 µA, P=14.4 W, average=3, skip=1, t=1 s, projections=1001, resolution=7,937 µm and an overall scan time of 67 min. A tomographic slice is seen in FIG. 2(b).

Example 3

Figure 3:
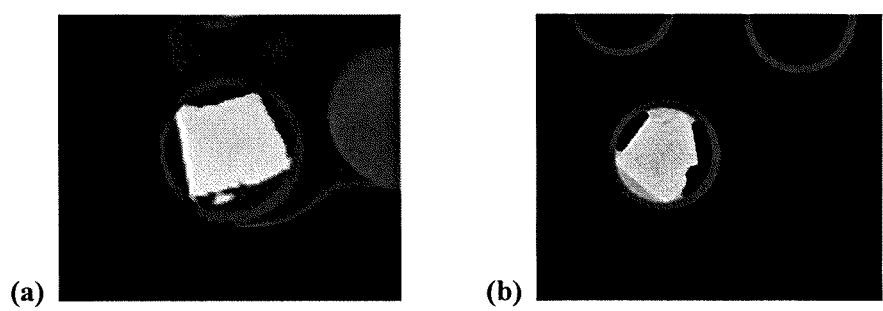
FIG. 3: (a) Turkey liver sample stained with the "in situ" staining method applying the gadolinium(III) chloride solution (332 mM) for 12 hours and hematein solution (332 mM) for 12 hours. (b) Turkey liver sample stained for 72 hours with the preformed gadolinium(III) hematein complex (working solution A (332 mM) and B (332 mM) were mixed before in a 1:1 ratio).

An in 1 vol/vol-% formaldehyde (FA, derived from a 37% acid free FA solution stabilized with ca. 10% methanol from Carl Roth) fixated turkey liver sample was placed in a sample container with a flat bottom holding 2 ml of working solution (A) containing 332 mM of hematein in absolute ethanol. The soft tissue sample was kept for 12 hours in the staining solution, which was placed on a horizontal rocking plate and kept in the dark. The soft tissue sample was removed with tweezers after 12 hours of staining and the residual staining solution was carefully removed with a cellulose tissue paper without pressing or modifying the soft tissue sample in any way. Then the soft tissue sample was placed in a new sample container with a flat bottom holding 2 ml of working solution (B) containing 332 mM gadolinium(III) chloride ($GdCl_3$) in distilled water. The soft tissue sample was kept for 12 hours in the staining solution, which was placed on a horizontal rocking plate and kept in the dark. The tissue sample was removed with tweezers after 12 hours of staining and the residual staining solution was carefully removed with a cellulose tissue paper without pressing or modifying the soft tissue sample in any way. The stained tissue sample was placed above 70 vol/vol-% ethanol vapor. The soft tissue sample was measured at a micro-computed tomography setup, the phoenix v|tome|x s 240 CT scanner from GE with the following parameters: U=50 kV, I=200 μA, P=10.0 W, average=2, skip=3, t=1 s, projections=1601, resolution=40.69 μm and an overall scan time of 134 min. A tomographic slice is seen in FIG. 3(a).

An in 1 vol/vol-% formaldehyde (FA, derived from a 37% acid free FA solution stabilized with ca. 10% methanol from Carl Roth) fixated turkey liver sample was placed in a sample container with a flat bottom holding 2 ml of a staining solution containing the hematein gadolinium(III) complex (a working solution (A) containing 332 mM of hematein in absolute ethanol and a working solution (B) containing 664 mM of $GdCl_3$ were mixed prior to adding the soft tissue sample in a ratio of 1:1). The tissue sample was kept for 72 hours in the staining solution, which was placed on a horizontal rocking plate and kept in the dark. The tissue sample was removed with tweezers after 72 hours of staining and the residual staining solution was carefully removed with a cellulose tissue paper without pressing or modifying the soft tissue sample in any way. The stained tissue sample was placed above 70 vol/vol-% ethanol vapor. The tissue sample was measured at a micro-computed tomography setup, the phoenix v|tome|x s 240 CT scanner from GE with the following parameters: U=50 kV, I=200 μA, P=10.0 W, average=2, skip=3, t=1 s, projections=1601, resolution=40.69 μm and an overall scan time of 134 min. A tomographic slice is shown in FIG. 3(b).

Example 4

To an in 4 vol/vol-% formaldehyde solution (FA, derived from a 37% acid free FA solution stabilized with ca. 10% methanol from Carl Roth) fixated pig liver sample were added 5% (vol./vol.) glacial acidic acid and the soft tissue sample was kept the fridge for 24 hours. Then the sample container (shown in FIG. 4a) with an inserted cone to create a flat bottom holding 0.3 ml of the working solution (B) containing 664 mM lead(II) acetate $(Pb(CH_3COO)_2)$ in distilled water. The soft tissue sample was kept in the dark at 25° C. (final staining result shown in FIG. 5a) or 35° C. (final staining result shown in FIG. 5b) for 72 hours in the staining solution, which was placed on a laboratory shaker (ThermoMixer from Eppendorf; 300 rpm; FIG. 4b). Then working solution (A) containing 332 mM of hematein in absolute ethanol was added to the same sample container resulting in an immediate color change to dark blue, which indicated complex formation. The soft tissue sample was kept in the dark at 25° C. (final staining result shown in FIG. 5c) or 35° C. (final staining result shown in FIG. 5d) for further 72 hours on a laboratory shaker (ThermoMixer from Eppendorf; 300 rpm; FIG. 4b) and kept in the dark. After staining, the soft tissue sample was removed with tweezers and the residual staining solution was carefully removed with a cellulose tissue paper without pressing or modifying the soft tissue sample in any way. The stained tissue sample was washed with tab water (6×0.3 ml) for 1 hour (in total 6 washes). As a last staining step, the soft tissue sample was placed in a new sample container with a flat bottom holding 0.3 ml of a 30 w/vol.-% eosin y solution in distilled water. The soft tissue sample was kept at 25° C. or 35° C. for 24 hours in the staining solution, which was placed in a laboratory shaker (ThermoMixer from Eppendorf; 300 rpm; FIG. 4b). After staining, the soft tissue sample was removed with tweezers and the residual staining solution was carefully removed with a cellulose tissue paper without pressing or modifying the soft tissue sample in any way. Finally, the soft tissue sample was placed above 70 vol/vol-% ethanol vapor. The soft tissue sample was measured at a micro-computed tomography (μCT) setup, the phoenix v|tome|x s 240 CT scanner from GE with the following parameters: U=50 kV, I=110 μA, P=5.5 W, time=1 s, average=3, skip=1, sensitivity=2.000, binning=1×1, projections=1601, resolution(t25)=69.508 μm, resolution(t35)=71.545 μm and an overall measurement time of 107 min A tomographic slice is shown in FIGS. 5a and 5b.

The line plots of the CT measurements of the stained soft tissue samples using the lead(II)-hematein complex stain and the eosin y stain, which were kept at 25° C., are shown in FIG. 5c and of the samples, which were kept at 35° C., are shown in FIG. 5d. Furthermore, a comparison of the line plots of the different temperatures is shown in FIG. 5e.

The invention claimed is:

1. An ex vivo method for investigating a biological sample comprising
   (aspect 1)
     (a1) staining the biological sample with a solution (AB) comprising one or more complex(es) comprising one or more heavy metal ion(s) M and one or more ligand(s) R, wherein:
       at least one M is a heavy metal ion having an atomic number of 23 or higher and 83 or lower, and
       at least one R is hematein; and
     (b) subjecting the stained biological sample to a computed tomography scanning method;
   or
   (aspect 2)
     (a2) staining the biological sample with
       (i) a solution (A) comprising hematein, and
       (ii) one or more solution(s) (B) comprising one or more heavy metal ion(s) wherein at least one M is a heavy metal ion having an atomic number of 23 or higher and 83 or lower,
       wherein the biological sample is contacted with solution (A) separately from the one or more solution(s) (B); and
     (b) subjecting the stained biological sample to a computed tomography scanning method.

2. The method according to claim 1, wherein the computed tomography scanning method of either aspect 1 or aspect 2 is an X-ray absorption-based scanning method.

3. The method according to claim 1, wherein the biological sample of either aspect 1 or aspect 2 is a human soft tissue sample.

4. The method according to claim 1, wherein the biological sample of either aspect 1 or aspect 2 is subjected to chemical fixation by means of one or more chemical fixative(s) prior to staining.

5. The method according to claim 4, wherein the one or more chemical fixative(s) comprise one or more acid(s).

6. The method according to claim 1, wherein the method of either aspect 1 or aspect 2 comprises, in addition to staining step (a1) or staining step (a2) an additional step of staining with an additional staining agent.

7. The method according to claim 1, wherein the concentration of complex-bound hematein in solution (AB) or of hematein in solution (A) is in the range of about 150 to about 500 mM.

8. The method according to claim 1 (aspect 2), wherein the time period of contacting the biological sample with solution (A) or the one or more solution(s) (B) is 1 hour or more.

9. The method according to claim 1 (aspect 2), wherein the biological sample is contacted with solution (A) before the biological sample is contacted with the one or more solution(s) (B).

10. The method according to claim 1 (aspect 2), wherein the main solvent of solution (A) is different to the main solvent of the one or more solution(s) (B).

11. The method according to claim 1, wherein the method of either aspect 1 or aspect 2 does not comprise, in addition to staining step (a1) or staining step (a2), an additional step of staining with an additional staining agent.

12. The method according to claim 1, wherein the at least one of the one or more heavy metal ion(s) M is an ion of a heavy metal selected from the group consisting of $Ag^{1+}$, $Ba^{2+}$, $Pb^{2+}$ or $Gd^{3+}$.

13. The method according to claim 2, wherein the computed tomography scanning method is Micro-Computed Tomography (μCT) or Nano-Computed Tomography (nanoCT).

14. The method according to claim 4, wherein the one or more chemical fixative(s) is/are a water-based formaldehyde solution or a water-based glutaraldehyde solution, or mixtures thereof.

15. The method according to claim 5, wherein the one or more acid(s) is glacial acetic acid.

16. The method according to claim 6, wherein the additional staining agent is a xanthene derivative selected from the group consisting of mono-, di-, tribromofluorescein; mono-, di, triiodofluorescein; eosin B; eosin Y and erythrosine B.

17. The method according to claim 10, wherein the main solvent of solutions (A) is ethanol, and the main solvent of the one or more solution(s) (B) is a water-based solution.

18. The method according to claim 1, wherein the complex is represented by the following formula (I):

$$M_mR_n \qquad (I),$$

in which
at least one M is a heavy metal ion having an atomic number of 23 or higher and 83 or lower,
at least one R is hematein, and
m and n are each independently 1, 2, 3, 4, 5, 6, 7, 8, 9, 10, 11 or 12.

19. The method according to claim 1, wherein at least one of the one or more heavy metal ion(s) M is an ion of a heavy metal selected from the group consisting of silver (Ag), barium (Ba), lead (Pb), gadolinium (Gd), bismuth (Bi), lutetium (Lu), lanthanum (La), and yttrium (Y).

20. The method according to claim 1, wherein at least one of the one or more heavy metal ion(s) M is an ion of a heavy metal selected from the group consisting of Pb, Ba, Gd, Y, Ag, Cu, Pt, Au, As, Sb, and Bi.

21. The method according to claim 1, wherein at least one of the one or more heavy metal ion(s) M is an ion of a heavy metal selected from the group consisting of transition metals having atomic numbers 23-28, 30; 40-46, 48, 72-77, and 80, and main group metals having atomic numbers 31, 32, 34, 37, 38, 49, 50, 52, 55, and 81.

* * * * *